US010362959B2

(12) United States Patent
Aiken et al.

(10) Patent No.: US 10,362,959 B2
(45) Date of Patent: Jul. 30, 2019

(54) SYSTEM AND METHOD FOR ASSESSING THE PROXIMITY OF AN ELECTRODE TO TISSUE IN A BODY

(75) Inventors: Robert D. Aiken, Stillwater, MN (US); D. Curtis Deno, Andover, MN (US); Glen H. Kastner, St. Michael, MN (US); Stephan P. Miller, Vadnais Heights, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 1166 days.

(21) Appl. No.: 12/465,337

(22) Filed: May 13, 2009

(65) Prior Publication Data
US 2009/0275827 A1 Nov. 5, 2009

Related U.S. Application Data

(63) Continuation-in-part of application No. 12/253,637, filed on Oct. 17, 2008, now Pat. No. 8,449,535, which
(Continued)

(51) Int. Cl.
*A61B 5/053* (2006.01)
*A61B 5/06* (2006.01)
(Continued)

(52) U.S. Cl.
CPC ............ *A61B 5/053* (2013.01); *A61B 5/0538* (2013.01); *A61B 5/06* (2013.01); *A61B 5/063* (2013.01);
(Continued)

(58) Field of Classification Search
CPC ....... A61B 5/053; A61B 5/06; A61B 18/1206; A61B 18/149; A61B 18/16;
(Continued)

(56) References Cited

U.S. PATENT DOCUMENTS 2,184,511 A 12/1939 Bango et al.
3,316,896 A 5/1967 Thomasset
(Continued)

FOREIGN PATENT DOCUMENTS

EP 1472976 11/2004
EP 1586281 4/2009
(Continued)

OTHER PUBLICATIONS

Cho, Sungbo et al., "Design of electrode array for impedance measurement of lesions in arteries".
(Continued)

*Primary Examiner* — Sujoy K Kundu
*Assistant Examiner* — L. Anderson
(74) *Attorney, Agent, or Firm* — Dykema Gossett PLLC

(57) ABSTRACT

A method and system for assessing proximity between an electrode and tissue is provided. The system includes an electronic control unit (ECU). The ECU is configured to acquire values for first and second components of a complex impedance between the electrode and the tissue, and to calculate an electrical coupling index (ECI) responsive to the first and second values. The ECU is further configured to process the ECI to determine the proximity of the electrode to the tissue. The ECU may be configured to calculate an electrical coupling index rate (ECIR) based on the calculated ECI and information relating to the change in location of the electrode, and to assess proximity based on the ECIR. Alternatively, the ECU may be configured to assess the proximity using the calculated ECI, as opposed to the ECIR.

44 Claims, 14 Drawing Sheets

Related U.S. Application Data is a continuation-in-part of application No. 12/095,688, filed as application No. PCT/US2006/061714 on Dec. 6, 2006, now Pat. No. 9,271,782.

(60) Provisional application No. 60/748,234, filed on Dec. 6, 2005.

(51) Int. Cl.
  *A61B 18/12* (2006.01)
  *A61B 18/14* (2006.01)
  *A61B 18/16* (2006.01)

(52) U.S. Cl.
  CPC .......... *A61B 5/068* (2013.01); *A61B 18/1206* (2013.01); *A61B 18/1492* (2013.01); *A61B 18/16* (2013.01); *A61B 2218/002* (2013.01)

(58) Field of Classification Search
  CPC ... A61B 2218/002; A61B 5/063; A61B 5/068; A61B 2018/0075; A61B 2018/00755; A61B 2018/00666; A61B 2018/00875; A61B 2018/00869; A61B 5/0538; A61B 18/1492; H01L 22/20; G02D 5/24482; G02D 5/2448
  USPC .......... 702/81, 82, 84, 94, 95, 152, 153, 168
  See application file for complete search history.

(56) References Cited

U.S. PATENT DOCUMENTS

| | | | |
|---|---|---|---|
| 3,949,736 A | 4/1976 | Vrana et al. |
| 4,641,649 A | 2/1987 | Walinsky et al. |
| 5,230,349 A | 7/1993 | Langberg |
| 5,257,635 A | 11/1993 | Langberg |
| 5,297,549 A | 3/1994 | Beatty et al. |
| 5,311,866 A | 5/1994 | Kagan et al. |
| 5,341,807 A | 8/1994 | Nardella |
| 5,366,896 A | 11/1994 | Margrey et al. |
| 5,423,808 A | 6/1995 | Edwards |
| 5,429,131 A | 7/1995 | Scheinman |
| 5,447,529 A | 9/1995 | Marchlinski et al. |
| 5,546,940 A | 8/1996 | Panescu et al. |
| 5,562,721 A | 10/1996 | Marchlinski et al. |
| 5,582,609 A | 12/1996 | Swanson |
| 5,588,432 A | 12/1996 | Crowley |
| 5,630,034 A | 5/1997 | Oikawa |
| 5,657,755 A | 8/1997 | Desai |
| 5,659,624 A | 8/1997 | Fazzari |
| 5,673,704 A | 10/1997 | Marchlinski et al. |
| 5,688,267 A | 11/1997 | Panescu |
| 5,697,377 A | 12/1997 | Wittkampf |
| 5,702,386 A | 12/1997 | Stern et al. |
| 5,718,241 A | 2/1998 | Ben-Haim et al. |
| 5,722,402 A | 3/1998 | Swanson |
| 5,730,127 A | 3/1998 | Avitall |
| 5,759,159 A | 6/1998 | Masreliez |
| 5,782,900 A | 7/1998 | de la Rama |
| 5,800,350 A | 9/1998 | Coppleson |
| 5,810,742 A | 9/1998 | Pearlman |
| 5,814,043 A | 9/1998 | Shapeton |
| 5,836,943 A | 11/1998 | Miller, III |
| 5,836,990 A | 11/1998 | Li |
| 5,837,001 A | 11/1998 | Mackey |
| 5,846,238 A | 12/1998 | Jackson et al. |
| 5,904,709 A | 5/1999 | Arndt |
| 5,944,022 A | 8/1999 | Nardella et al. |
| 5,954,665 A | 9/1999 | Ben-Haim |
| 6,001,093 A | 12/1999 | Swanson |
| 6,019,757 A | 2/2000 | Scheldrup |
| 6,026,323 A | 2/2000 | Skladnev |
| 6,035,341 A | 3/2000 | Nunally |
| 6,063,078 A | 5/2000 | Wittkampf |
| 6,129,669 A * | 10/2000 | Panescu et al. .............. 600/424 |
| 6,171,304 B1 | 1/2001 | Netherly |
| 6,179,824 B1 | 1/2001 | Eggers |
| 6,206,874 B1 | 3/2001 | Ubby |
| 6,217,574 B1 | 4/2001 | Webster |
| 6,217,576 B1 | 4/2001 | Tu |
| 6,221,070 B1 | 4/2001 | Tu et al. |
| 6,226,542 B1 | 5/2001 | Reisfeld |
| 6,233,476 B1 | 5/2001 | Strommer et al. |
| 6,246,896 B1 | 6/2001 | Dumoulin et al. |
| 6,256,540 B1 | 7/2001 | Panescu et al. |
| 6,322,558 B1 | 11/2001 | Taylor et al. |
| 6,337,994 B1 | 1/2002 | Stoianovici |
| 6,391,024 B1 | 5/2002 | Sun |
| 6,423,057 B1 | 7/2002 | He et al. |
| 6,427,089 B1 | 7/2002 | Knowlton |
| 6,443,894 B1 | 9/2002 | Sumanaweera et al. |
| 6,445,952 B1 * | 9/2002 | Manrodt et al. ................. 607/28 |
| 6,456,864 B1 | 9/2002 | Swanson et al. |
| 6,471,693 B1 | 10/2002 | Carroll et al. |
| 6,475,215 B1 | 11/2002 | Tanrisever |
| 6,490,474 B1 | 12/2002 | Willis |
| 6,498,944 B1 | 12/2002 | Ben-Haim et al. |
| 6,507,751 B2 | 1/2003 | Blume et al. |
| 6,511,478 B1 | 1/2003 | Burnside et al. |
| 6,546,270 B1 | 4/2003 | Goldin et al. |
| 6,558,382 B2 | 5/2003 | Jahns et al. |
| 6,569,160 B1 | 5/2003 | Goldin |
| 6,575,969 B1 | 6/2003 | Rittman, III et al. |
| 6,605,082 B2 | 8/2003 | Hareyama |
| 6,652,518 B2 | 11/2003 | Wellman |
| 6,663,622 B1 | 12/2003 | Foley |
| 6,676,654 B1 | 1/2004 | Balle-Petersen et al. |
| 6,683,280 B1 | 1/2004 | Wofford |
| 6,690,963 B2 | 2/2004 | Ben-Haim et al. |
| 6,696,844 B2 | 2/2004 | Wong et al. |
| 6,712,074 B2 | 3/2004 | Edwards |
| 6,743,225 B2 | 6/2004 | Sanchez et al. |
| 6,755,790 B2 | 6/2004 | Stewart |
| 6,780,182 B2 | 8/2004 | Bowman |
| 6,788,967 B2 | 9/2004 | Ben-Haim et al. |
| 6,813,515 B2 | 11/2004 | Hashimshony |
| 6,840,938 B1 | 1/2005 | Morley et al. |
| 6,917,834 B2 | 7/2005 | Koblish et al. |
| 6,918,876 B1 | 7/2005 | Kamiyama |
| 6,926,669 B1 | 8/2005 | Stewart |
| 6,936,047 B2 | 8/2005 | Nasab et al. |
| 6,950,689 B1 | 9/2005 | Willis |
| 6,964,867 B2 | 11/2005 | Downs |
| 6,965,795 B2 | 11/2005 | Rock |
| 6,993,384 B2 * | 1/2006 | Bradley et al. ................... 607/2 |
| 7,041,096 B2 | 5/2006 | Malis et al. |
| 7,106,043 B1 | 9/2006 | Da Silva |
| 7,197,354 B2 | 3/2007 | Sobe |
| 7,248,032 B1 | 7/2007 | Hular |
| 7,263,395 B2 | 8/2007 | Chan et al. |
| 7,263,397 B2 | 8/2007 | Hauck et al. |
| 7,386,339 B2 | 6/2008 | Strommer et al. |
| 7,497,858 B2 | 3/2009 | Chapelon et al. |
| 7,499,745 B2 | 3/2009 | Littrup |
| 7,536,218 B2 * | 5/2009 | Govari et al. ................. 600/424 |
| 7,565,613 B2 | 7/2009 | Forney |
| 7,610,078 B2 | 10/2009 | Willis |
| 7,633,502 B2 | 12/2009 | Willis |
| 7,671,871 B2 | 3/2010 | Gonsalves |
| 7,776,034 B2 | 8/2010 | Kampa |
| 7,819,870 B2 | 10/2010 | Thao et al. |
| 7,865,236 B2 | 1/2011 | Cory et al. |
| 7,904,174 B2 * | 3/2011 | Hammill et al. .............. 607/116 |
| 7,925,349 B1 | 4/2011 | Wong et al. |
| 7,953,495 B2 | 5/2011 | Sommer et al. |
| 8,075,498 B2 | 12/2011 | Leo et al. |
| 8,403,925 B2 | 3/2013 | Miller |
| 2001/0034501 A1 | 10/2001 | Tom |
| 2001/0039413 A1 | 11/2001 | Bowe |
| 2001/0047129 A1 | 11/2001 | Hall |
| 2001/0051774 A1 | 12/2001 | Littrup et al. |
| 2002/0013537 A1 | 1/2002 | Rock |
| 2002/0022836 A1 | 2/2002 | Goble |
| 2002/0049375 A1 | 4/2002 | Strommer et al. |

(56) References Cited

U.S. PATENT DOCUMENTS

| | | |
|---|---|---|
| 2002/0068931 A1 | 6/2002 | Wong |
| 2002/0072686 A1 | 6/2002 | Hoey et al. |
| 2002/0077627 A1 | 6/2002 | Johnson et al. |
| 2002/0120188 A1* | 8/2002 | Brock et al. .................. 600/407 |
| 2002/0123749 A1 | 9/2002 | Jain |
| 2002/0177847 A1 | 11/2002 | Long |
| 2003/0028183 A1 | 2/2003 | Sanchez et al. |
| 2003/0045871 A1 | 3/2003 | Jain et al. |
| 2003/0060696 A1 | 3/2003 | Skladnev et al. |
| 2003/0065364 A1 | 4/2003 | Wellman et al. |
| 2003/0093067 A1 | 5/2003 | Panescu et al. |
| 2003/0093069 A1 | 5/2003 | Panescu |
| 2003/0100823 A1 | 5/2003 | Kipke |
| 2003/0109871 A1 | 6/2003 | Johnson et al. |
| 2003/0130711 A1 | 7/2003 | Pearson et al. |
| 2003/0187430 A1 | 10/2003 | Vorisek |
| 2004/0006337 A1 | 1/2004 | Nasab et al. |
| 2004/0030258 A1 | 2/2004 | Williams et al. |
| 2004/0044292 A1 | 3/2004 | Yashushi |
| 2004/0078036 A1 | 4/2004 | Keidar |
| 2004/0078058 A1 | 4/2004 | Holmstrom |
| 2004/0082946 A1 | 4/2004 | Malis et al. |
| 2004/0087975 A1 | 5/2004 | Lucatero |
| 2004/0097806 A1 | 5/2004 | Hunter |
| 2004/0147920 A1 | 7/2004 | Keidar |
| 2004/0181165 A1 | 9/2004 | Hoey et al. |
| 2004/0243018 A1* | 12/2004 | Organ et al. .................. 600/547 |
| 2004/0243181 A1 | 12/2004 | Conrad et al. |
| 2004/0267252 A1 | 12/2004 | Washington |
| 2005/0010263 A1* | 1/2005 | Schauerte ................. 607/48 |
| 2005/0054944 A1 | 3/2005 | Nakada |
| 2005/0065507 A1 | 3/2005 | Hartley |
| 2005/0222554 A1 | 10/2005 | Wallace |
| 2006/0015033 A1* | 1/2006 | Blakley et al. .............. 600/509 |
| 2006/0085049 A1 | 4/2006 | Cory et al. |
| 2006/0116669 A1 | 6/2006 | Dolleris |
| 2006/0173251 A1 | 8/2006 | Govari |
| 2006/0200049 A1 | 9/2006 | Leo et al. |
| 2006/0235286 A1 | 10/2006 | Stone |
| 2007/0016006 A1 | 1/2007 | Shachar |
| 2007/0055142 A1 | 3/2007 | Webler |
| 2007/0073179 A1 | 3/2007 | Afonso et al. |
| 2007/0083193 A1 | 4/2007 | Werneth et al. |
| 2007/0100332 A1 | 5/2007 | Paul et al. |
| 2007/0106269 A1 | 5/2007 | O'Sullivan |
| 2007/0106289 A1 | 5/2007 | O'Sullivan |
| 2007/0123764 A1 | 5/2007 | Thao et al. |
| 2007/0161915 A1 | 7/2007 | Desai |
| 2007/0225558 A1 | 9/2007 | Hauck |
| 2007/0225593 A1 | 9/2007 | Porath |
| 2007/0244479 A1 | 10/2007 | Beatty et al. |
| 2007/0255162 A1 | 11/2007 | Abboud et al. |
| 2008/0091193 A1 | 4/2008 | Kauphusman |
| 2008/0097220 A1 | 4/2008 | Lieber |
| 2008/0097422 A1 | 4/2008 | Edwards |
| 2008/0132890 A1 | 6/2008 | Woloszko |
| 2008/0183071 A1 | 7/2008 | Strommer et al. |
| 2008/0183189 A1 | 7/2008 | Teichman et al. |
| 2008/0221440 A1 | 9/2008 | Iddan et al. |
| 2008/0234564 A1 | 9/2008 | Beatty et al. |
| 2008/0249536 A1 | 10/2008 | Stahler |
| 2008/0275465 A1 | 11/2008 | Paul et al. |
| 2008/0288023 A1 | 11/2008 | John |
| 2008/0288038 A1 | 11/2008 | Paul |
| 2008/0300589 A1 | 12/2008 | Paul et al. |
| 2008/0312713 A1 | 12/2008 | Wilfley et al. |
| 2009/0012533 A1 | 1/2009 | Barbagli |
| 2009/0036794 A1 | 2/2009 | Stubhaug et al. |
| 2009/0163904 A1 | 6/2009 | Miller et al. |
| 2009/0171235 A1 | 7/2009 | Schneider |
| 2009/0171345 A1 | 7/2009 | Miller et al. |
| 2009/0177111 A1 | 7/2009 | Miller |
| 2009/0247942 A1 | 10/2009 | Kirschenman |
| 2009/0247943 A1 | 10/2009 | Kirschenman |
| 2009/0247944 A1 | 10/2009 | Kirschenman |
| 2009/0247993 A1 | 10/2009 | Kirschenman et al. |
| 2009/0248042 A1 | 10/2009 | Kirschenman |
| 2009/0275827 A1 | 11/2009 | Aiken et al. |
| 2009/0276002 A1 | 11/2009 | Sommer et al. |
| 2009/0306655 A1 | 12/2009 | Stangenes |
| 2010/0069921 A1 | 3/2010 | Miller et al. |
| 2010/0168550 A1 | 7/2010 | Byrd |
| 2010/0168735 A1 | 7/2010 | Deno et al. |
| 2010/0191089 A1 | 7/2010 | Stebler et al. |
| 2010/0256558 A1 | 10/2010 | Olson et al. |
| 2010/0274239 A1 | 10/2010 | Paul et al. |
| 2010/0298823 A1 | 11/2010 | Cao et al. |
| 2011/0015569 A1 | 1/2011 | Kirschenman |
| 2011/0118727 A1 | 5/2011 | Fish |
| 2011/0313311 A1 | 12/2011 | Gaw |
| 2011/0313417 A1 | 12/2011 | De La Rama et al. |
| 2012/0158011 A1* | 6/2012 | Sandhu et al. ................ 606/130 |

FOREIGN PATENT DOCUMENTS

| | | |
|---|---|---|
| JP | 3585491 | 12/1996 |
| JP | 2005-279256 | 10/2005 |
| WO | 1998/046149 | 10/1998 |
| WO | 2000/078239 | 12/2000 |
| WO | 2007067628 | 6/2007 |
| WO | WO-2007067941 | 6/2007 |
| WO | 2009065140 | 5/2009 |
| WO | WO-2009/065140 | 5/2009 |
| WO | 2009/085457 | 7/2009 |
| WO | 2009/120982 | 10/2009 |
| WO | 2011/123669 | 10/2011 |

OTHER PUBLICATIONS

Fenici, R. R. et al., "Biomagnetically localizable multipurpose catheter and method for MCG guided intracardiac electrophysiology, biopsy and ablation of cardiac arrhythmias", *Int'l Journal of Cardiac Imaging*.

Gales, Rosemary et al., "Use of bioelectrical impedance analysis to assess, body composition of seals".

Masse, Stephane et al., "A Three-dimensional display for cardiac activation mapping", *Pace*, vol. 14 Apr. 1991.

Salazar, Y et al., "Transmural versus nontransmural in situ electrical impedance spectrum for healthy, ischemic, and healed myocardium".

"International Search Report & Written Opinion", PCT/US2011/047235 dated Dec. 14, 2011.

Chakraborty, D. P., "ROC curves predicted by a model of visual search", *Institute of Physics Publishing, Phys. Med. Biol.* 51 2006, 3463-3482.

Gao, Xin et al., "Computer-Assisted Quantative Evaluation of Therapeutic Responses for Lymphoma Using Serial PET/CT Imaging", *NIH Public Access, Acad Radiol.* 17(4) Apr. 2010, 1-21.

Himel, Herman D., "Development of a metric to assess completeness of lesions produced by radiofrequency ablation in the heart", *Dept. of Biomedical Engineering, University of NC, Chapel Hill* 2006, i-xvii; 1-138.

International Search Report and Written Opinion of the International Search Authority for International Application No. PCT/US2010/034412 dated Jun. 29, 2010.

International Preliminary Report on Patentability for for International Application No. PCT/US2010/034412 dated Nov. 15, 2011.

Extended European Search Report for International Application No. PCT/US2010/034412 dated Oct. 25, 2013.

Title: International Search Report and Written Opinion of the International Searching Authority Citation: PCT/US2006/061714 Publication Date: Sep. 22, 2008.

International Search Report and Written Opinion in PCT Application No. PCT/US2008/084194 (dated Feb. 5, 2009).

Supplementary European Search Report issued in EP Patent Application No. 11842330.0 (dated Jan. 20, 2014).

Avitall, Boaz; "The Effects of Electrode-Tissue Contact on Radiofrequency Lesion Generation"; PACE, vol. 20; Reference pp. 2899-2910; Publication Date: Dec. 1997.

(56) References Cited

OTHER PUBLICATIONS

Dumas, John H.; "Myocardial electrical impedance as a predictor of the quality of RF-induced linear lesions"; Physiological Measurement, vol. 29; Reference Pages: Abstract only; Publication Date: Sep. 17, 2008.
Gao, Xin; "Computer-Assisted Quantative Evaluation of Therapeutic Responses for Lymphoma Using Serial PET/CT Imaging", NIH Public Access, Acad Radiol. 17(4); Reference pp. 1-21; Publication Date: Apr. 2010.
He, Ding Sheng; "Assessment of Myocardial Lesion Size during In Vitro Radio Frequency Catheter Ablation"; IEEE Transactions on Biomedical Engineering, vol. 50, No. 6; Reference pp. 768-776; Publication Date: Jun. 2003.
Holmes, Douglas; "Tissue Sensing Technology Enhances Lesion Formation During Irrigated Catheter Ablation"; HRS; Reference Pages: Abstract only; Publication Date: 2008.
International Search Report and Written Opinion in PCT/US2011/047235 (dated Dec. 14, 2011).
Zheng, Xiangsheng; "Electrode Impedance: An Indicator of Electrode-Tissue Contact and Lesion Dimensions During Linear Ablation"; Journal of Interventional Cardiac Electrophysiology 4; Reference pp. 645-654; Publication Date: Dec. 2000.
Thomas, Stuart P., et al., Comparison of Epicardial and Endocardial Linear Ablation Using Handheld Probes, The Annals of Thoracic Surgery, vol. 75, Issue 2, pp. 543-548, Feb. 2003.
International Search Report for PCT Application No. PCT/US2006/046565, dated May 2, 2007. 1 page.
International Search Report and Written Opinion for PCT Application No. PCT/US2006/061716, dated Oct. 4, 2007. 7 pages.
International Search Report and Written Opinion for PCT Application No. PCT/US2006/061712, dated Oct. 29, 2007, 7 pages.
International Search Report and Written Opinion for PCT Application No. PCT/US2006/061710, dated Feb. 15, 2008. 10 pages.
International Search Report and Written Opinion for PCT Application No. PCT/US2006/061711, dated Oct. 5, 2007. 8 pages.
International Search Report and Written Opinion for PCT Application No. PCT/US2006/061713, dated Oct. 3, 2007. 1 page.
International Search Report and Written Opinion for PCT Application No. PCT/US2006/061717, dated Oct. 4, 2007. 9 pages.
Supplementary European Search Report for EP Application No. 06839102.8, dated Nov. 16, 2009. 7 pages.
Supplementary European Search Report for EP Application No. 06848530.9, dated Nov. 17, 2009. 7 pages.
Supplementary European Search Report for EP Application No. 06840133.0, dated Nov. 16, 2009. 8 pages.
International Search Report and Written Opinion for PCT Application No. PCT/US2008/084200, dated Jan. 22, 2009. 1 page.
International Search Report and Written Opinion for PCT Application No. PCT/US2010/034414, dated Sep. 1, 2010. 13 pages.

\* cited by examiner

SYSTEM AND METHOD FOR ASSESSING THE PROXIMITY OF AN ELECTRODE TO TISSUE IN A BODY

This application is a continuation-in-part of U.S. patent application Ser. No. 12/253,637 filed Oct. 17, 2008, the entire disclosure of which is incorporated by reference, which is a continuation-in-part of U.S. patent application Ser. No. 12/095,688 filed May 30, 2008, the entire disclosure of which is also incorporated herein by reference. U.S. patent application Ser. No. 12/095,688 is a national stage application of, and claims priority to, International Application No. PCT/US2006/061714 filed Dec. 6, 2006, the entire disclosure of which is incorporated herein by reference. The International Application was published in the English language on Jun. 14, 2007 as International Publication No. WO 2007/067941 A2 and itself claims the benefit of U.S. Provisional Patent Application No. 60/748,234 filed Dec. 6, 2005, the entire disclosure of which is incorporated herein by reference.

BACKGROUND OF THE INVENTION a. Field of the Invention

This invention relates to a system and method for assessing the proximity of an electrode to tissue in a body. In particular, the instant invention relates to a system and method for assessing the proximity of electrodes on a diagnostic and/or therapeutic medical device, such as a mapping or ablation catheter, and tissue, such as cardiac tissue.

b. Background Art

Electrodes are used on a variety of diagnostic and/or therapeutic medical devices. For example, electrodes may be used on cardiac mapping catheters to generate an image of the internal geometry of a heart and electrical potentials within the tissue. Electrodes are also used on ablation catheters to create tissue necrosis in cardiac tissue to correct conditions such as atrial arrhythmia (including, but not limited to, ectopic atrial tachycardia, atrial fibrillation, and atrial flutter). Arrhythmia can create a variety of dangerous conditions including irregular heart rates, loss of synchronous atrioventricular contractions and stasis of blood flow which can lead to a variety of ailments and even death. It is believed that the primary cause of atrial arrhythmia is stray electrical signals within the left or right atrium of the heart. The ablation catheter imparts ablative energy (e.g., radiofrequency energy, cryoablation, lasers, chemicals, high-intensity focused ultrasound, etc.) to cardiac tissue to create a lesion in the cardiac tissue. This lesion disrupts undesirable electrical pathways and thereby limits or prevents stray electrical signals that lead to arrhythmias.

The safety and effectiveness of many of diagnostic and/or therapeutic devices is often determined in part by the proximity of the device and the electrodes to the target tissue. In mapping catheters, the distance between the electrodes and the target tissue affects the strength of the electrical signal and the identity of the mapping location. The safety and effectiveness of ablation lesions is determined in part by the proximity of the ablation electrode to target tissue and the effective application of energy to that tissue. If the electrode is too far from the tissue or has insufficient contact with the tissue, the lesions created may not be effective. On the other hand, if the catheter tip containing the electrode contacts the tissue with excessive force, the catheter tip may perforate or otherwise damage the tissue (e.g., by overheating). It is therefore beneficial to assess the quality of contact between the electrode and the tissue, as well as the proximity of the electrode to the tissue.

While in many conventional systems catheter position and speed are known, knowledge relating to the proximity of a catheter electrode to tissue, or contact therebetween, is somewhat challenging. These challenges arise, at least in part, from the precision required and factors such as posture of the patient, ventilation, and cardiac contraction. Assessing proximity and contact in these known systems, such as, for example, robotic applications, has typically been based on discrete force measurements using various devices such as, for example, strain gauges, fiber optics, or pressure inducers. While such techniques may be useful in sensing or assessing the existence and magnitude or degrees of contact between the electrode and the tissue, they present disadvantages with respect to assessing proximity of the electrode to the tissue.

One major drawback of using such techniques to assess proximity is that proximity information cannot be determined until after contact with the tissue has been made. Accordingly, these techniques do not provide the necessary information until it is effectively too late, since contact has already been made and proximity information post-contact is essentially useless. As such, the proximity information cannot be used to indicate to the user or robot that the electrode is in "close proximity" to the tissue, and allow the user or robot to adjust their conduct (e.g., speed of approach, angle of approach, etc.) accordingly.

The inventors herein have recognized a need for a system and method for assessing or sensing the proximity of a catheter electrode to tissue that will minimize and/or eliminate one or more of the above-identified deficiencies.

BRIEF SUMMARY OF THE INVENTION

The present invention is directed to a method and system for assessing proximity between an electrode and tissue. The system according to the present teachings includes an electronic control unit (ECU). The ECU is configured to acquire values for first and second components of a complex impedance between the electrode and the tissue. The ECU is further configured to calculate an electrical coupling index (ECI) responsive to the first and second values. The ECU is still further configured to process the calculated ECI to determine the proximity of the electrode to the tissue.

In an exemplary embodiment, the ECU is further configured to receive location coordinates corresponding to a location of the electrode within the body, to calculate a change in the ECI over a predetermined period of time, to calculate a change in the location coordinates of the electrode of the same predetermined period of time, and to calculate an electrical coupling index rate (ECIR) by dividing the change in the ECI by the change in the location coordinates of the electrode.

In another exemplary embodiment, however, the ECU is further configured to assess the proximity of the electrode to the tissue using the calculated ECI, as opposed to the ECIR.

In accordance with another aspect of the invention, an article of manufacture is provided. The article of manufacture includes a storage medium having a computer program encoded thereon for assessing the proximity of the electrode to the tissue. The computer program includes code for calculating an ECI responsive to values for first and second components of a complex impedance between the electrode and the tissue, and processing the calculated ECI to determine whether the electrode is within a predetermined distance from the tissue.

Finally, in accordance with yet another aspect of the invention, a method for assessing the proximity of an electrode to the tissue is provided. The method includes first step of acquiring values for first and second components of a complex impedance between the electrode and the tissue. In a second step, an ECI responsive to the first and second values is calculated. A third step includes processing the calculated ECI to determine whether the electrode is within a predetermined distance from the tissue.

The foregoing and other aspects, features, details, utilities, and advantages of the present invention will be apparent from reading the following description and claims, and from reviewing the accompanying drawings.

DETAILED DESCRIPTION OF EMBODIMENTS OF THE INVENTION

Figure 1:
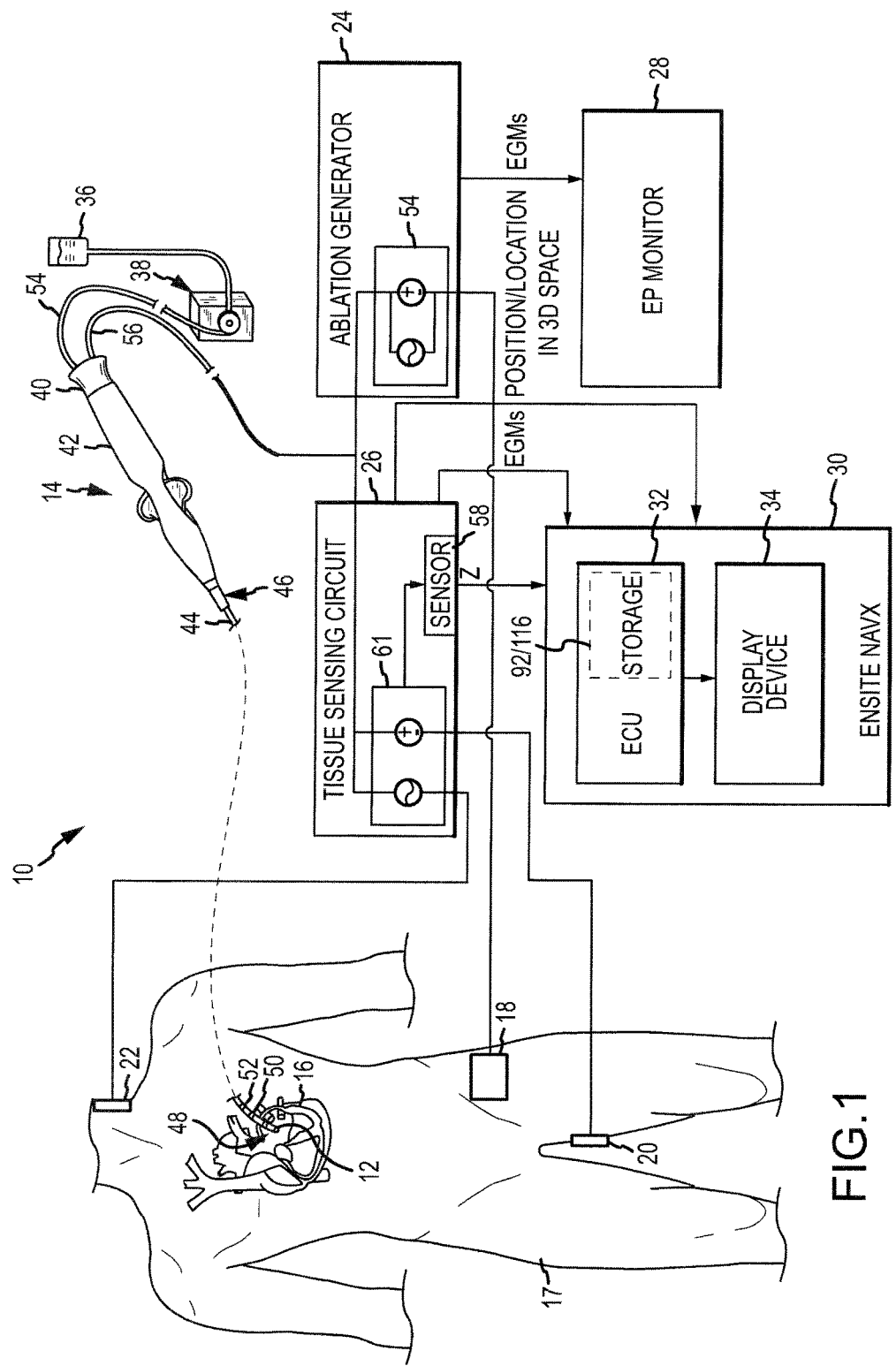
FIG. 1 is diagrammatic view of a system in accordance with the present teachings.

Referring now to the drawings wherein like reference numerals are used to identify identical components in the various views, FIG. 1 illustrates one embodiment of a system 10 for one or more diagnostic and therapeutic functions including components providing an improved assessment of, among other things, a degree of coupling between an electrode 12 on a catheter 14 and a tissue 16 in a body 17. As will be described in greater detail below, the degree of coupling can be useful for assessing, among other things, the degree of contact between the electrode 12 and the tissue 16, as well as the relative proximity of the electrode 12 to the tissue 16. In the illustrated embodiment, the tissue 16 comprises heart or cardiac tissue. It should be understood, however, that the present invention may be used to evaluate coupling between electrodes and a variety of body tissues. Further, although the electrode 12 is illustrated as part of the catheter 14, it should be understood that the present invention may be used to assess a degree of coupling between any type of electrode and tissue including, for example, intracardiac electrodes, needle electrodes, patch electrodes, wet brush electrodes (such as the electrodes disclosed in commonly assigned U.S. patent application Ser. No. 11/190,724 filed Jul. 27, 2005, the entire disclosure of which is incorporated herein by reference) and virtual electrodes (e.g., those formed from a conductive fluid medium such as saline including those disclosed in commonly assigned U.S. Pat. No. 7,326,208 issued Feb. 5, 2008, the entire disclosure of which is incorporated herein by reference). In addition to the catheter 14, the system 10 may include patch electrodes 18, 20, 22, an ablation generator 24, a tissue sensing circuit 26, an electrophysiology (EP) monitor 28, and a system 30 for visualization, mapping and navigation of internal body structures which may include an electronic control unit 32 in accordance with the present invention and a display device 34 among other components.

The catheter 14 is provided for examination, diagnosis and treatment of internal body tissues such as the tissue 16. In accordance with one embodiment of the invention, the catheter 14 comprises an ablation catheter and, more particularly, an irrigated radio-frequency (RF) ablation catheter. It should be understood, however, that the present invention can be implemented and practiced regardless of the type of ablation energy provided (e.g., cryoablation, ultrasound, etc.) In an exemplary embodiment, the catheter 14 is connected to a fluid source 36 having a biocompatible fluid such as saline through a pump 38 (which may comprise, for example, a fixed rate roller pump or variable volume syringe pump with a gravity feed supply from the fluid source 36 as shown) for irrigation. It should be noted, however, that the present invention is not meant to be limited to irrigated catheters, but rather it finds applicability in any number of catheter-based applications. In an exemplary embodiment, the catheter 14 is also electrically connected to the ablation generator 24 for delivery of RF energy. The catheter 14 may include a cable connector or interface 40, a handle 42, a shaft 44 having a proximal end 46 and a distal 48 end (as used herein, "proximal" refers to a direction toward the end of the catheter near the clinician, and "distal" refers to a direction away from the clinician and (generally) inside the body of a patient) and one or more electrodes 12, 50, 52. The catheter 14 may also include other conventional components not illustrated herein such as a temperature sensor, additional electrodes, and corresponding conductors or leads.

The connector 40 provides mechanical, fluid and electrical connection(s) for cables 54, 56 extending from the pump 38 and the ablation generator 24. The connector 40 is conventional in the art and is disposed at a proximal end of the catheter 14.

The handle 42 provides a location for the clinician to hold the catheter 14 and may further provides means for steering or the guiding shaft 44 within the body 17. For example, the handle 42 may include means to change the length of a guidewire extending through the catheter 14 to the distal end 48 of the shaft 44 to steer the shaft 44. The handle 42 is also conventional in the art and it will be understood that the construction of the handle 42 may vary. In an alternate exemplary embodiment, the catheter 14 may be robotically driven or controlled. Accordingly, rather than a clinician manipulating a handle to steer or guide the catheter 14, and the shaft 44 thereof, in particular, a robot is used to manipulate the catheter 14.

The shaft 44 is an elongated, tubular, flexible member configured for movement within the body 17. The shaft 44 support the electrodes 12, 50, 52, associated conductors, and possibly additional electronics used for signal processing or conditioning. The shaft 44 may also permit transport, delivery and/or removal of fluids (including irrigation fluids and bodily fluids), medicines, and/or surgical tools or instruments. The shaft 44 may be made from conventional materials such as polyurethane and defines one or more lumens configured to house and/or transport electrical conductors, fluids or surgical tools. The shaft 44 may be introduced into a blood vessel or other structure within the body 17 through a conventional introducer. The shaft 44 may then be steered or guided through the body 17 to a desired location such as the tissue 16 with guidewires or other means known in the art.

The electrodes 12, 50, 52 are provided for a variety of diagnostic and therapeutic purposes including, for example, electrophysiological studies, catheter identification and location, pacing, cardiac mapping and ablation. In the illustrated embodiment, the catheter 14 includes an ablation tip electrode 12 at the distal end 48 of the shaft 44, and a pair of ring electrodes 50, 52. It should be understood, however, that the number, shape, orientation and purpose of the electrodes 12, 50, 52 may vary.

The patch electrodes 18, 20, 22 provide RF or navigational signal injection paths and/or are used to sense electrical potentials. The electrodes 18, 20, 22 may also have additional purposes such as the generation of an electromechanical map. The electrodes 18, 20, 22 are made from flexible, electrically conductive material and are configured for affixation to the body 17 such that the electrodes 18, 20, 22 are in electrical contact with the patient's skin. The electrode 18 may function as an RF indifferent/dispersive return for the RF ablation signal. The electrodes 20, 22 may function as returns for the RF ablation signal source and/or an excitation signal generated by the tissue sensing circuit 26 as described in greater detail hereinbelow. In accordance with one aspect of the present invention discussed hereinbelow, the electrodes 20, 22 are preferably spaced relatively far apart. In the illustrated embodiment, the electrodes 20, 22, are located on the medial aspect of the left leg and the dorsal aspect of the neck. The electrodes 20, 22, may alternatively be located on the front and back of the torso or in other conventional orientations.

The ablation generator 24 generates, delivers, and controls RF energy output by the ablation catheter 14. The generator 24 is conventional in the art and may comprise the commercially available unit sold under the model number IBI-1500T RF Cardiac Ablation Generator, available from Irvine Biomedical, Inc. The generator 24 includes an RF ablation signal source 54 configured to generate an ablation signal that is output across a pair of source connectors: a positive polarity connector SOURCE (+) which may connect to the tip electrode 12; and a negative polarity connector SOURCE(−) which may be electrically connected by conductors or lead wires to one of the patch electrodes 18, 20, 22 (see FIG. 2). It should be understood that the term connectors as used herein does not imply a particular type of physical interface mechanism, but is rather broadly contemplated to represent one or more electrical nodes. The source 54 is configured to generate a signal at a predetermined frequency in accordance with one or more user specified parameters (e.g., power, time, etc.) and under the control of various feedback sensing and control circuitry as is know in the art. The source 54 may generate a signal, for example, with a frequency of about 450 kHz or greater. The generator 24 may also monitor various parameters associated with the ablation procedure including impedance, the temperature at the tip of the catheter, ablation energy and the position of the catheter and provide feedback to the clinician regarding these parameters. The impedance measurement output by the generator 24, however, reflects the magnitude of impedance not only at the tissue 16, but the entire impedance between the tip electrode 12 and the corresponding patch electrode 18 on the body surface. The impedance output by the generator 24 is also not easy to interpret and correlate to tissue contact by the clinician. In an exemplary embodiment, the ablation generator 24 may generate a higher frequency current for the purposes of RF ablation, and a second lower frequency current for the purpose of measuring impedance.

The tissue sensing circuit 26 provides a means, such as a tissue sensing signal source 61, for generating an excitation signal used in impedance measurements and means, such as a complex impedance sensor 58, for resolving the detected impedance into its component parts. The signal source 61 is configured to generate an excitation signal across source connectors SOURCE (+) and SOURCE (−) (See FIG. 2). The source 61 may output a signal having a frequency within a range from about 1 kHz to over 500 kHz, more preferably within a range of about 2 kHz to 200 kHz, and even more preferably about 20 kHz. In one embodiment, the excitation signal is a constant current signal, preferably in the range of between 20-200 µA, and more preferably about 100 µA. As discussed below, the constant current AC excitation signal generated by the source 61 is configured to develop a corresponding AC response voltage signal that is dependent on the complex impedance of the tissue 16 and is sensed by the complex impedance sensor 58. The sensor 58 resolves the complex impedance into its component parts (i.e., the resistance (R) and reactance (X) or the impedance magnitude (|Z|) and phase angle ($\angle Z$ or $\varphi$)). Sensor 58 may include conventional filters (e.g., bandpass filters) to block frequencies that are not of interest, but permit appropriate frequencies, such as the excitation frequency, to pass, as well as conventional signal processing software used to obtain the component parts of the measured complex impedance.

It should be understood that variations are contemplated by the present invention. For example, the excitation signal may be an AC voltage signal where the response signal comprises an AC current signal. Nonetheless, a constant current excitation signal is preferred as being more practical. It should be appreciated that the excitation signal frequency is preferably outside of the frequency range of the RF ablation signal, which allows the complex impedance sensor 58 to more readily distinguish the two signals, and facilitates filtering and subsequent processing of the AC response voltage signal. The excitation signal frequency is also preferably outside the frequency range of conventionally expected electrogram (EGM) signals in the frequency range of 0.05 Hz-1 kHz. Thus, in summary, the excitation signal preferably has a frequency that is preferably above the typical EGM signal frequencies and below the typical RF ablation signal frequencies.

The circuit 26 is also connected, for a purpose described hereinbelow, across a pair of sense connectors: a positive polarity connector SENSE (+) which may connect to the tip electrode 12; and a negative polarity connector SENSE (−) which may be electrically connected to one of the patch electrodes 18, 20, 22 (see FIG. 2; note, however, that the connector SENSE (−) should be connected to a different electrode of the electrodes 18, 20, 22 relative to the connector SOURCE (−) as discussed below). It should again be understood that the term connectors as used herein does not imply a particular type of physical interface mechanism, but is rather broadly contemplated to represent one or more electrical nodes.

Figure 2:
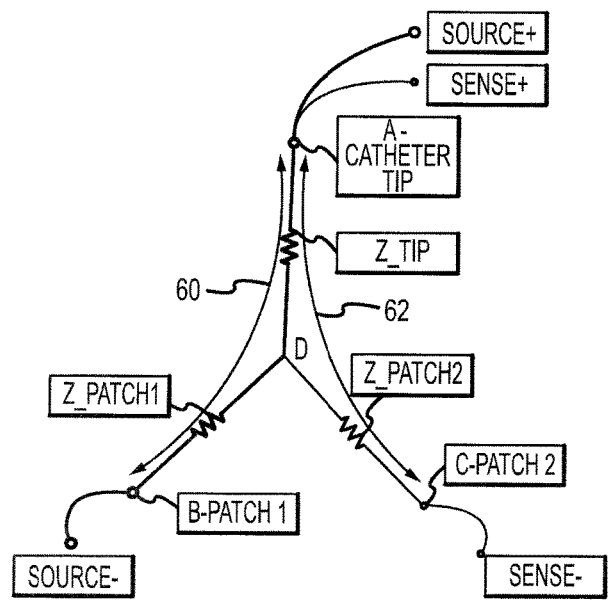
FIG. 2 is a simplified schematic diagram illustrating how impedance is determined in accordance with the present teachings.

Referring now to FIG. 2, connectors SOURCE (+), SOURCE (−), SENSE (+) and SENSE (−) form a three terminal arrangement permitting measurement of the complex impedance at the interface of the tip electrode 12 and the tissue 16. Complex impedance can be expressed in rectangular coordinates as set forth in equation (1):

$$Z = R + jX \quad (1)$$

where R is the resistance component (expressed in ohms); and X is a reactance component (also expressed in ohms). Complex impedance can also be expressed polar coordinates as set forth in equation (2):

$$Z = r \cdot e^{j\varphi} = |Z| \cdot e^{j\angle Z} \quad (2)$$

where |Z| is the magnitude of the complex impedance (expressed in ohms) and $\angle Z = \varphi$ is the phase angle expressed in radians. Alternatively, the phase angle may be expressed in terms of degrees where $$\phi = \left(\frac{180}{\pi}\right)\theta.$$

Throughout the remainder of this specification, phase angle will be preferably referenced in terms of degrees. The three terminals comprise: (1) a first terminal designated "A-Catheter Tip" which is the tip electrode 12; (2) a second terminal designated "B-Patch 1" such as the source return patch electrode 22; and (3) a third terminal designated "C-Patch 2" such as the sense return patch electrode 20. In addition to the ablation (power) signal generated by the source 54 of the ablation generator 24, the excitation signal generated by the source 61 in the tissue sensing circuit 26 is also be applied across the source connectors (SOURCE (+), SOURCE(−)) for the purpose of inducing a response signal with respect to the load that can be measured and which depends on the complex impedance. As described above, in one embodiment, a 20 kHz, 100 µA AC constant current signal is sourced along a path 60, as illustrated, from one connector (SOURCE (+), starting at node A) through the common node (node D) to a return patch electrode (SOURCE (−), node B). The complex impedance sensor 58 is coupled to the sense connectors (SENSE (+), SENSE (−)), and is configured to determine the impedance across a path 62. For the constant current excitation signal of a linear circuit, the impedance will be proportional to the observed voltage developed across SENSE (+)/SENSE(−), in accordance with Ohm's Law: Z=V/I. Because voltage sensing is nearly ideal, the current flows through the path 60 only, so the current through the path 62 (node D to node C) due to the excitation signal is effectively zero. Accordingly, when measuring the voltage along the path 62, the only voltage observed will be where the two paths intersect (i.e., from node A to node D). Depending on the degree of separation of the two patch electrodes (i.e., those forming nodes B and C), an increasing focus will be placed on the tissue volume nearest the tip electrode 12. If the patch electrodes are physically close to each other, the circuit pathways between the catheter tip electrode 12 and the patch electrodes will overlap significantly and impedance measured at the common node (i.e., node D) will reflect impedances not only at the interface of the catheter electrode 12 and the tissue 16, but also other impedances between the tissue 16 and the surface of body 17. As the patch electrodes are moved further apart, the amount of overlap in the circuit paths decreases and impedance measured at the common node is only at or near the tip electrode 12 of the catheter 14.

Figure 3:
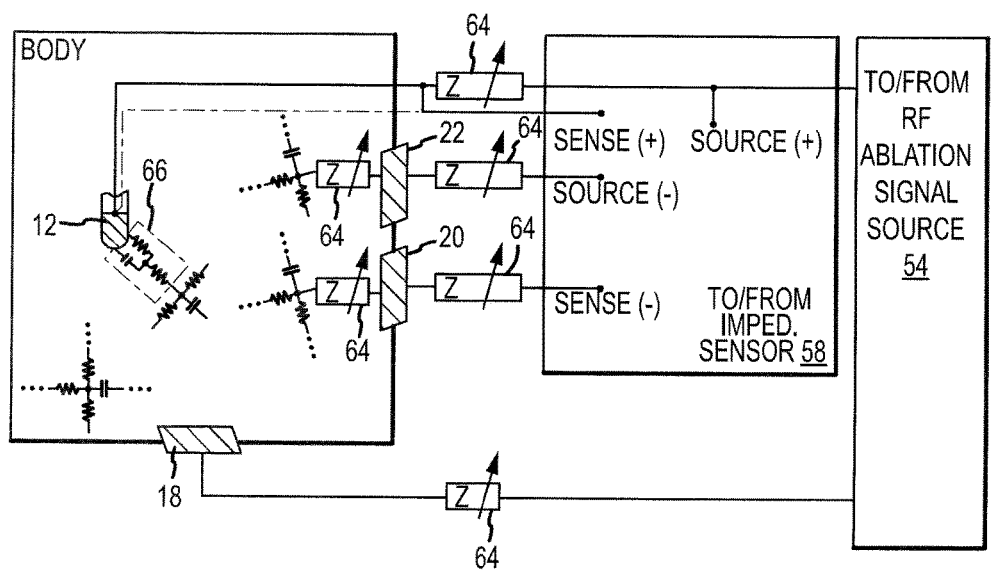
FIG. 3 is a diagrammatic and block diagram illustrating the approach in FIG. 2 in greater detail.

Referring now to FIG. 3, the concept illustrated in FIG. 2 is extended. FIG. 3 is a simplified schematic and block diagram of the three-terminal measurement arrangement of the invention. For clarity, it should be pointed out that the SOURCE (+) and SENSE (+) lines may be joined in the catheter connector 40 or the handle 42 (as in solid line) or may remain separate all the way to the tip electrode 12 (the SENSE (+) line being shown in phantom line from the handle 42 to the tip electrode 12). FIG. 3 shows, in particular, several sources of complex impedance variations, shown generally as blocks 64, that are considered "noise" because such variations do not reflect the physiologic changes in the tissue 16 or electrical coupling whose complex impedance is being measured. For reference, the tissue 16 whose complex impedance is being measured is that near and around the tip electrode 12 and is enclosed generally by a phantom-line box 66 (and the tissue 16 is shown schematically, in simplified form, as a resistor/capacitor combination). One object of the invention is to provide a measurement arrangement that is robust or immune to variations that are not due to changes in or around the box 66. For example, the variable complex impedance boxes 64 that are shown in series with the various cable connections (e.g., in the SOURCE (+) connection, in the SOURCE (−) and SENSE (−) connections, etc.) may involve resistive/inductive variations due to cable length changes, cable coiling and the like. The variable complex impedance boxes 64 that are near the patch electrodes 20, 22, may be more resistive/capacitive in nature, and may be due to body perspiration and the like over the course of a study. As will be seen, the various arrangements of the invention are relatively immune to the variations in the blocks 64, exhibiting a high signal-to-noise (S/N) ratio as to the complex impedance measurement for the block 66.

Although the SOURCE (−) and SENSE (−) returns are illustrated in FIG. 3 as patch electrodes 20, 22, it should be understood that other configurations are possible. In particular, the indifferent/dispersive return electrode 18 can be used as a return as well as another electrode 50, 52 on the catheter 14, such as the ring electrode 50 as described in commonly assigned U.S. patent application Ser. No. 11/966,232 filed on Dec. 28, 2007 and titled "SYSTEM AND METHOD FOR MEASUREMENT OF AN IMPEDANCE USING A CATHETER SUCH AS AN ABLATION CATHETER," the entire disclosure of which is incorporated herein by reference.

The EP monitor 28 is provided to display electrophysiology data including, for example, an electrogram. The monitor 28 is conventional in the art and may comprise an LCD or CRT monitor or another conventional monitor. The monitor 28 may receive inputs from the ablation generator 24 as well as other conventional EP lab components not shown in the illustrated embodiment.

The system 30 is provided for visualization, mapping, and navigation of internal body structures. The system 30 may comprise the system having the model name EnSite NavX™ and commercially available from St. Jude Medical., Inc. and as generally shown with reference to commonly assigned U.S. Pat. No. 7,263,397 titled "Method and Apparatus for Catheter Navigation and Location and Mapping in the Heart," the entire disclosure of which is incorporated herein by reference. The system 30 may include the electronic control unit (ECU) 32 and the display device 34 among other components. However, in another exemplary embodiment, the ECU 32 is a separate and distinct component that is electrically connected to the system 30.

The ECU 32 is provided to acquire values for first and second components of a complex impedance between the catheter tip electrode 12 and the tissue 16 and to calculate an electrical coupling index (ECI) responsive to the values with the coupling index indicative of a degree of coupling between the electrode 12 and the tissue 16. The ECU 32 preferably comprises a programmable microprocessor or microcontroller, but may alternatively comprise an application specific integrated circuit (ASIC). The ECU 32 may include a central processing unit (CPU) and an input/output (I/O) interface through which the ECU 32 may receive a plurality of input signals including signals from the sensor 58 of the tissue sensing circuit 26 and generate a plurality of output signals including those used to control the display device 34. In accordance with one aspect of the present invention, the ECU 32 may be programmed with a computer program (i.e., software) encoded on a computer storage medium for determining a degree of coupling between the electrode 12 on the catheter 14 and the tissue 16 in the body 17. The program includes code for calculating an ECI responsive to values for first and second components of the complex impedance between the catheter electrode 12 and the tissue 16 with the ECI indicative of a degree of coupling between the catheter electrode 12 and the tissue 16.

The ECU 32 acquires one or more values for two component parts of the complex impedance from signals generated by the sensor 58 of the tissue sensing circuit 26 (i.e., the resistance (R) and reactance (X) or the impedance magnitude ($|Z|$) and phase angle ($\varphi$) or any combination of the foregoing or derivatives or functional equivalents thereof). In accordance with one aspect of the present invention, the ECU 32 combines values for the two components into a single ECI that provides an improved measure of the degree of coupling between the electrode 12 and the tissue 16 and, in particular, the degree of electrical coupling between the electrode 12 and the tissue 16. As will be described in greater detail below, the single ECI may provide an improved measure of the proximity of the electrode 12 relative to the tissue 16.

Validation testing relating to the coupling index was performed in a pre-clinical animal study. The calculated coupling index was compared to pacing threshold as an approximation of the degree of coupling. Pacing threshold was used for comparison because it is objective and particularly sensitive to the degree of physical contact between the tip electrode and tissue when the contact forces are low and the current density paced into the myocardium varies. In a study of seven swine (n=7, 59+/−3 kg), a 4 mm tip irrigated RF ablation catheter was controlled by an experienced clinician who scored left and right atrial contact at four levels (none, light, moderate and firm) based on clinician sense, electrogram signals, three-dimensional mapping, and fluoroscopic images. Several hundred pacing threshold data points were obtained along with complex impedance data, electrogram amplitudes and data relating to clinician sense regarding contact. A regression analysis was performed using software sold under the registered trademark "MINITAB" by Minitab, Inc. using the Log 10 of the pacing threshold as the response and various impedance parameters as the predictor. The following table summarizes the results of the analysis:

| Model | Regression Factors in Model | | | | | Regression $\hat{R}^2$ | |
|---|---|---|---|---|---|---|---|
| | | | | | | $\hat{R}^2$ | $\hat{R}^2\_adj$ |
| 1 | | | | | R1_mean ($p < 0.001$) | 43.60% | 43.50% |
| 2 | | | | | X1_mean ($p < 0.001$) | 35.70% | 35.50% |
| 3 | | | | X1_mean ($p < 0.001$) | R1_mean ($p < 0.001$) | 47.20% | 46.90% |
| 4 | | X1_stdev ($p = 0.300$) | R1_stdev ($p = 0.155$) | X1_mean ($p < 0.001$) | R1_mean ($p < 0.001$) | 48.70% | 48.00% |
| 5 | R1_P-P ($p = 0.253$) | X1_stdev ($p = 0.280$) | R1_stdev ($p = 0.503$) | X1_mean ($p < 0.001$) | R1_mean ($p < 0.001$) | 49.00% | 48.10% |

As shown in the table, it was determined that a mean value for resistance accounted for 43.5% of the variation in pacing threshold while a mean value for reactance accounted for 35.5% of the variation in pacing threshold. Combining the mean resistance and mean reactance values increased the predictive power to 46.90% demonstrating that an ECI based on both components of the complex impedance will yield improved assessment of coupling between the catheter electrode 12 and the tissue 16. As used herein, the "mean value" for the resistance or reactance may refer to the average of N samples of a discrete time signal $x_i$ or a low-pass filtered value of a continuous $x(t)$ or discrete $x(t_i)$ time signal. As shown in the table, adding more complex impedance parameters such as standard deviation and peak to peak magnitudes can increase the predictive power of the ECI. As used herein, the "standard deviation" for the resistance or reactance may refer to the standard deviation, or equivalently root mean square (rms) about the mean or average of N samples of a discrete time signal $x_i$ or the square root of a low pass filtered value of a squared high pass filtered continuous $x(t)$ or discrete $x(t_i)$ time signal. The "peak to peak magnitude" for the resistance or reactance may refer to the range of the values over the previous N samples of the discrete time signal $x_i$ or the $k^{th}$ root of a continuous time signal $[abs(x(t))]^k$ that has been low pass filtered for sufficiently large $k>2$. It was further determined that, while clinician sense also accounted for significant variation in pacing threshold (48.7%)—and thus provided a good measure for assessing coupling—the combination of the ECI with clinician sense further improved assessment of coupling (accounting for 56.8% of pacing threshold variation).

Because of the processing and resource requirements for more complex parameters such as standard deviation and peak to peak magnitude, and because of the limited statistical improvement these parameters provided, it was determined that the most computationally efficient ECI would be based on mean values of the resistance (R) and reactance (X). From the regression equation, the best prediction of pacing threshold—and therefore coupling—was determined to be the following equation (3):

$$ECI = Rmean - 5.1 * Xmean \qquad (3)$$

where Rmean is the mean value of a plurality of resistance values and Xmean is the mean value of a plurality of reactance values. It should be understood, however, that other values associated with the impedance components, such as a standard deviation of a component or peak to peak magnitude of a component which reflect variation of impedance with cardiac motion or ventilation, can also serve as useful factors in the ECI. Further, although the above equation and following discussion focus on the rectangular coordinates of resistance (R) and reactance (X), it should be understood that the ECI could also be based on values associated with the polar coordinates impedance magnitude ($|Z|$) and phase angle ($\varphi$) or indeed any combination of the foregoing components of the complex impedance and derivatives or functional equivalents thereof. Finally, it should be understood that coefficients, offsets and values within the equation for the ECI may vary depending on, among other things, the desired level or predictability, the species being treated, and disease states. In accordance with the present invention, however, the coupling index will always be responsive to both components of the complex impedance in order to arrive at an optimal assessment of coupling between the catheter electrode 12 and the tissue 16.

The above-described analysis was performed using a linear regression model wherein the mean value, standard deviation, and/or peak to peak magnitude of components of the complex impedance were regressed against pacing threshold values to enable determination of an optimal ECI. It should be understood, however, that other models and factors could be used. For example, a nonlinear regression model may be used in addition to, or as an alternative to, the linear regression model. Further, other independent measures of tissue coupling such as atrial electrograms could be used in addition to, or as an alternative to, pacing thresholds.

Validation testing was also performed in a human trial featuring twelve patients undergoing catheter ablation for atrial fibrillation. The patients were treated using an irrigated, 7 French radio frequency (RF) ablation catheter with a 4 mm tip electrode operating at a standard setting of a 50° C. tip temperature, 40 W power, and 30 ml/min. flow rate (adjusted accordingly proximate the esophagus). An experienced clinician placed the catheter in the left atrium in positions of unambiguous non-contact and unambiguous contact (with varying levels of contact including "light," "moderate," and "firm") determined through fluoroscopic imaging, tactile feedback electrograms, clinician experience, and other information. In addition to impedance, measurements of electrogram amplitudes and pacing thresholds were obtained for comparison. Each measure yielded corresponding changes in value as the catheter electrode moved from a no-contact position to a contact position. In particular, electrogram amplitudes increased from 0.14+/−0.16 to 2.0+/−1.9 mV, pacing thresholds decreased from 13.9+/−3.1 to 3.1+/−20 mA and the ECI increased from 118+/−15 to 145+/−24 (with resistance increasing from 94.7+/−11.0 to 109.3+/−15.1Ω and reactance decreasing from −4.6+/−0.9 to −6.9+/−2Ω). Further, the ECI increased (and resistance increased and reactance decreased) as the catheter electrode was moved from a "no-contact" (115+/−12) position to "light," (135+/−15) "moderate," (144+/−17) and "firm" (159+/−34) positions. These measurements further validate the use of the ECI to assess coupling between the catheter electrode 12 and the tissue 16. The calculated ECI and clinician sense of coupling were again compared to pacing threshold as an approximation of the degree of coupling. A regression analysis was performed using a logarithm of the pacing threshold as the response and various impedance parameters and clinician sense as predictors. From this analysis, it was determined that clinician sense accounted for approximately 47% of the variability in pacing threshold. The addition of the ECI, however, with clinician sense resulted in accounting for approximately 51% of the variability in pacing threshold—further demonstrating that the ECI can assist clinicians in assessing coupling between the catheter electrode 12 and the tissue 16.

Figure 4:
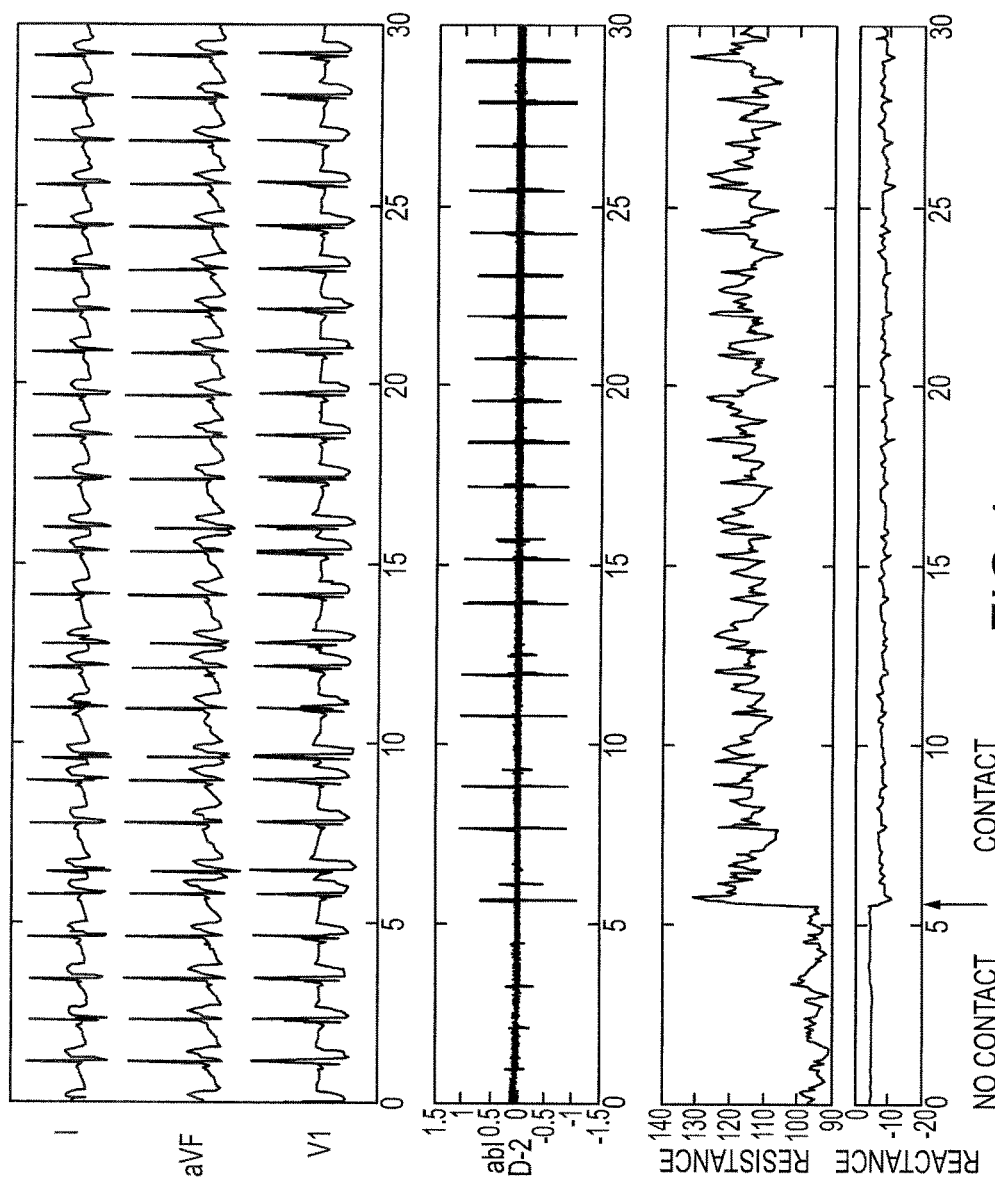
FIG. 4 is a series of diagrams illustrating complex impedance variations during atrial tissue ablation and cardiac tissue contact over thirty (30) seconds.
Figure 5:
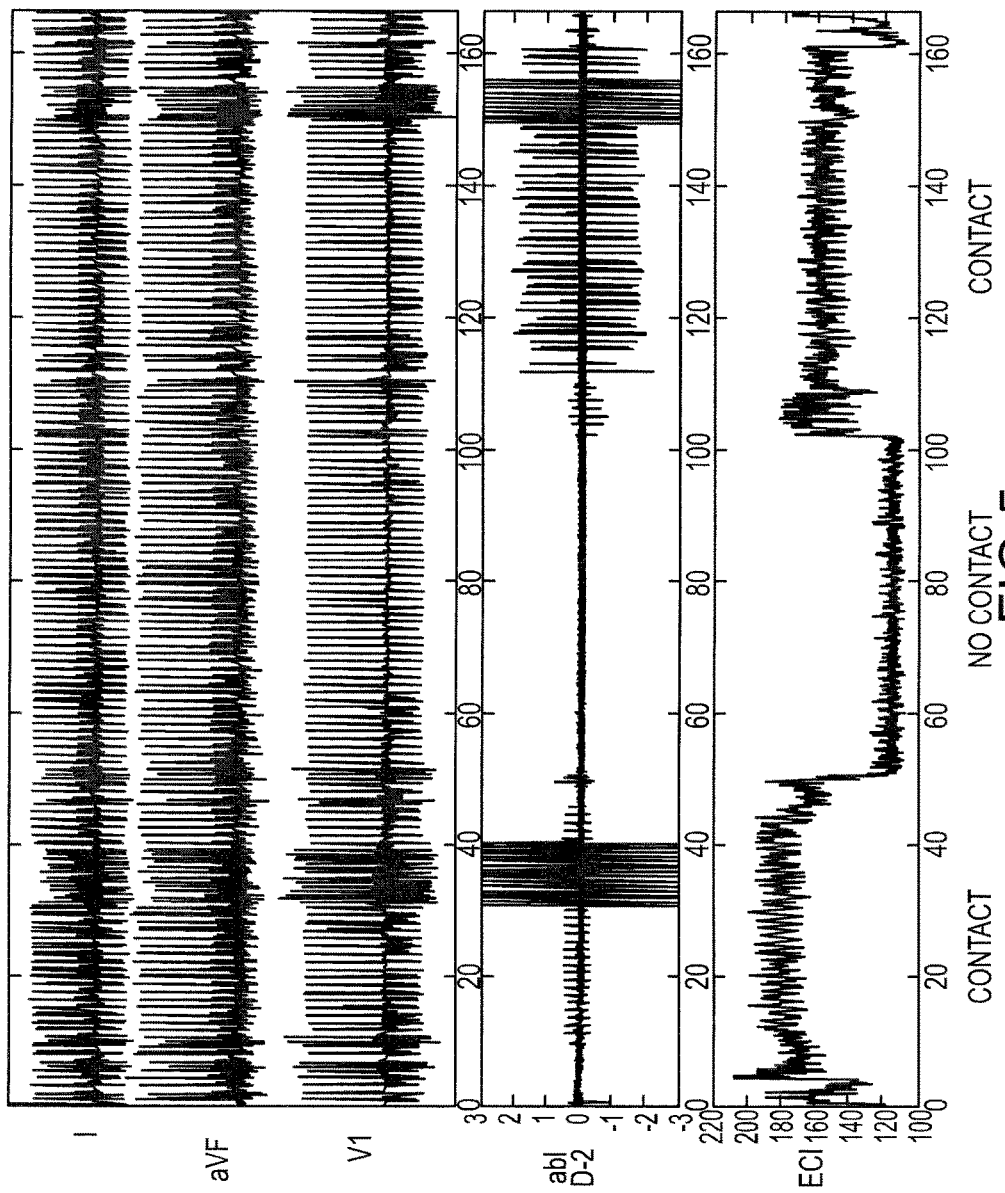
FIG. 5 is a series of diagrams illustrating variations in a coupling index during atrial tissue ablation and cardiac tissue contact over one hundred and sixty (160) seconds.

Referring now to FIGS. 4-5, a series of timing diagrams (in registration with each other) illustrate a comparison of atrial electrograms relative to changes in resistance and reactance (FIG. 4) and the composite ECI (FIG. 5). As noted hereinabove, atrial electrograms are one traditional measurement for assessing coupling between the catheter electrode 12 and the tissue 16. As shown in FIG. 4, the signal amplitude of the atrial electrogram (labeled "ABL D-2" in FIG. 4) increases when the catheter electrode 12 moves from a position of "no contact" to "contact" with the tissue 16. Similarly, measured resistance (R) increases and reactance (X) decreases and become more variable (FIG. 4) and the calculated ECI increases (FIG. 5), further demonstrating the utility of the ECI in assessing coupling between the electrode 12 and the tissue 16.

The human validation testing also revealed that the ECI varied depending on tissue types. For example, the ECI tended to be higher when the catheter electrode was located inside a pulmonary vein than in the left atrium. As a result, in accordance with another aspect of the present invention, the ECI may be used in identifying among tissue types (e.g., to identify vascular tissue as opposed to trabeculated and myocardial tissue). Further, because force sensors may not adequately estimate the amount of energy delivered into tissue in constrained regions, such as the pulmonary vein or trabeculae, the inventive ECI may provide a more meaningful measure of ablation efficacy than force sensors. In addition, in certain situations, it may be advantageous to utilize both a force sensor and the ECI.

Impedance measurements are also influenced by the design of the catheter 14, the connection cables 56, or other factors. Therefore, the ECI may preferably comprise a flexible equation in which coefficients and offsets are variable in response to design parameters associated with the catheter 14. The catheter 14 may include a memory such as an EEPROM that stores numerical values for the coefficients and offsets or stores a memory address for accessing the numerical values in another memory location (either in the catheter EEPROM or in another memory). The ECU 32 may retrieve these values or addresses directly or indirectly from the memory and modify the ECI accordingly.

The physical structure of the patient is another factor that may influence impedance measurements and the ECI. Therefore, the ECU 32 may also be configured to offset or normalize the ECI (e.g., by adjusting coefficients or offsets within the index) responsive to an initial measurement of impedance or another parameter in a particular patient. In addition, it may be beneficial to obtain and average values for the ECI responsive to excitation signals generated by the source 61 at multiple different frequencies.

Figure 6:
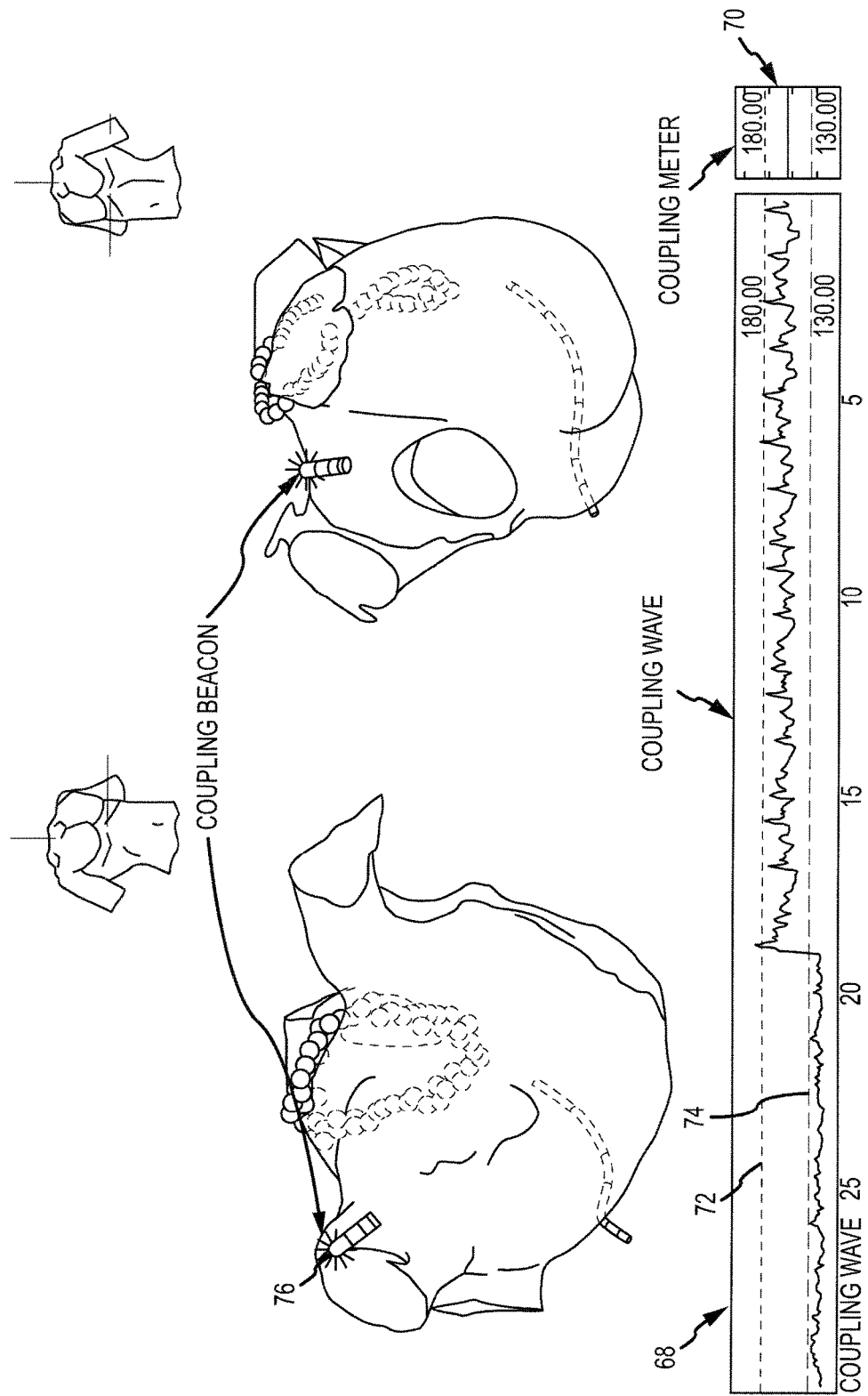
FIG. 6 is a screen display illustrating possible formats for presenting a coupling index to a clinician.

Referring now to FIG. 6, the display device 34 is provided to present the ECI in a format useful to the clinician. The device 34 may also provide a variety of information relating to visualization, mapping, and navigation, as is known in the art, including measures of electrical signals, two and three dimensional images of the tissue 16, and three-dimensional reconstructions of the tissue 16. The device 34 may comprise an LCD monitor or other conventional display device. In accordance with another aspect of the present invention, the ECI may be displayed in one or more ways to provide easy interpretation and correlation to tissue contact and/or proximity of the electrode 12 to the tissue 16 for the clinician. Referring to FIG. 6, the ECI may be displayed as a scrolling waveform 68. The ECI may also be displayed as a meter 70 which displays the one second average value of the ECI. For either the scrolling waveform 68 or the meter 70, upper and lower thresholds 72, 74 may be set (either pre-programmed in the ECU 32 or input by the user using a conventional I/O device). Characteristics of the waveform 68 and/or the meter 70 may change depending upon whether the value of the ECI is within the range set by the thresholds (e.g., the waveform 68 or the meter 70 may change colors, such as from green to red, if the value of the ECI moves outside of the range defined by the thresholds). Changes to the ECI may also be reflected in changes to the image of the catheter 14 and/or the catheter electrode 12 on the display device 34. For example, the catheter electrode 12 may be displayed on the screen (including within a two or three dimensional image or reconstruction of the tissue) as a beacon 76. Depending on the value of the ECI, the appearance of the beacon 76 may change. For example, the color of the beacon 76 may change (e.g., from green to red) and/or lines may radiate outwardly from the beacon 76 as the index falls above, below or within a range of values. In another exemplary embodiment, the length of the splines of the beacon 76 may continuously vary with the ECI.

In summary, the degree of coupling between a catheter electrode 12 and the tissue 16, which may be used to assess the proximity of the electrode 12 to the tissue 16, may be assessed through several method steps in accordance with one embodiment of the invention. First, an excitation signal is applied between the electrode 12 and a reference electrode such as the patch electrode 22 between connectors SOURCE (+) and SOURCE (−) along the first path 60 (see FIG. 2). As discussed above, the signal source 61 of the tissue sensing circuit 26 may generate the excitation signal at a predetermined frequency or frequencies. This action induces a voltage along the path 62 between the electrode 12 and another reference electrode such as the patch electrode 20. The voltage may be measured by the sensor 58 which resolves the sensed voltage into component parts of the complex impedance at the tissue 16. As a result, the ECU 32 acquires values for the components of the complex impedance. The ECU 32 then calculates a ECI responsive to the values that is indicative of a degree of coupling between the electrode 12 and the tissue 16. The index may then be presented to a clinician in a variety of forms including by display on the display device 34 as, for example, the waveform 68, the meter 70, or the beacon 76.

An ECI formed in accordance with the teaching of the present invention may be useful in a variety of applications. As shown in the embodiment illustrated in FIG. 1, the ECI can be used as part of the system 10 for ablation of the tissue 16. The ECI provides an indication of the degree of electrical coupling between the tip electrode 12 and the tissue 16, thereby assisting in the safe and effective delivery of ablation energy to the tissue 16.

The ECI may further provide an indication of the proximity or orientation of the tip electrode 12 to the adjacent tissue 16. Referring to FIGS. 1 and 2, the signal source 61 of the sensing circuit 26 may generate excitation signals across source connectors SOURCE (+) and SOURCE (−) defined between the tip electrode 12 and the patch electrode 22, and also between the ring electrode 50 and the patch electrode 22. The impedance sensor 58 may then measure the resulting voltages across sense connectors SENSE (+) and SENSE (−)) defined between the tip electrode 12 and the patch electrode 20, and also between the ring electrode 50 and the patch electrode 22. In an exemplary embodiment, the measurements for the tip 12 and the ring 50 are taken at different frequencies or times. The ECU 32 may compare the measured values directly or, more preferably, determine an ECI for each of the electrodes 12, 50 responsive to the measured values, and compare the two ECIs. Differences between the measured impedance or ECI for the electrodes 12, 50 may indicate that the electrode 12 is disposed at an angle (as well as the degree of that angle) relative to the tissue 16.

It should be understood that the electrode 50 is used for exemplary purposes only. Similar results could be obtained with other electrodes disposed proximate the tip electrode 12 or from using a split tip electrode. For example, in another exemplary embodiment, the ECI may provide an indication of proximity or orientation of the catheter's tip to adjacent tissue by employing two or more electrodes near the tip. In one such embodiment, the tip electrode 12 is used together with and adjacent the ring electrode 50 to provide two independent measures of complex impedance and ECI. This is accomplished in the manner described with respect to FIGS. 1-3, but relies on separate SOURCE and SENSE circuits and connections that operate on different frequencies, or that are time division multiplexed to achieve independence. Cutaneous patch electrodes 20, 22 may be used in common for both tip and ring electrode impedance and ECU determinations. The ECU 32 may employ the two impedance measurements directly or operate on the difference of the impedances or ECIs. When in non-contact and of a defined proximity region, the tip and ring ECIs will both be constant and exhibit a fixed difference (depending on electrode design). Changes in this differential impedance or ECI reflect proximity of one (or both) electrodes to tissue. Once the tip electrode is in contact, the value of the differential ECI may indicate the angle of incidence of the catheter tip with tissue. Similar results could be obtained from other electrodes disposed near the tip electrode 12 or from using a split-tip electrode.

As briefly described above, the present invention may also be used as a proximity sensor to assess or determine the proximity of the electrode 12 to the tissue 16. As an electrode, such as the electrode 12, approaches the tissue 16, the impedance changes as does the ECI. The ECI is therefore indicative of the proximity of the electrode 12 to the tissue 16. In some applications, the general position (with a frame of reference) and speed of the tip of the catheter 14 and the electrode 12 is known (although the proximity of the electrode 12 to the tissue 16 is unknown). As will be described in greater detail below, this information can be combined to define a value (the "electrical coupling index rate" or ECIR) that is indicative of the rate of change in the ECI as the electrode 12 approaches the tissue 16 and which may provide an improved measure of the proximity of the electrode 12 to the tissue 16. This information can be used, for example, in robotic catheter applications to slow the rate of approach prior to contact, and also in connection with a transseptal access sheath having a distal electrode to provide an indication that the sheath is approaching (and/or slipping away from) the septum.

Figure 7:
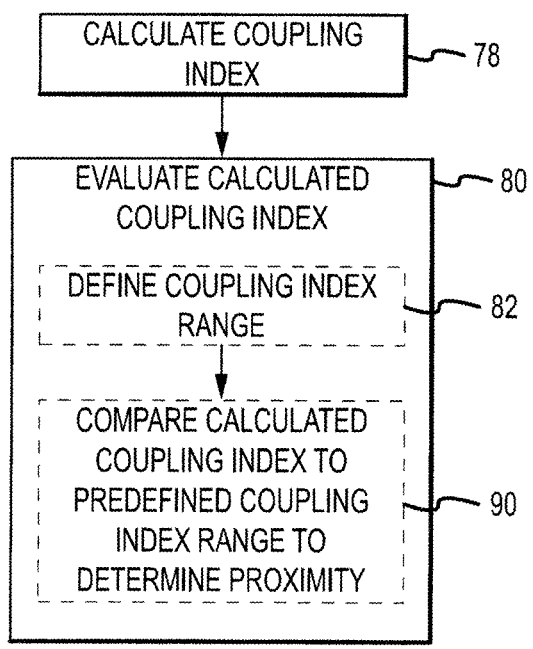
FIG. 7 is a flow diagram illustrative of an exemplary embodiment of a method for assessing the proximity of an electrode to tissue in accordance with present teachings.

In exemplary embodiment, the raw calculated ECI may be used to assess the proximity of the electrode 12 to the tissue 16. This particular embodiment provides a relatively simple discrimination of proximity. The ECU 32 calculates the ECI as described in detail above. The calculated ECI may then be used to assess the proximity of the electrode 12 to the tissue 16. FIG. 7 illustrates an exemplary embodiment of a method for assessing the proximity using the ECI.

In this particular embodiment, a current ECI is calculated in a first step 78. In a second step 80, the calculated ECI is evaluated to determine whether the electrode 12 is within a predetermined distance from the tissue 16, in contact with the tissue 16, or further away from the tissue 16 than the predetermined distance. More particularly, in a first substep 82 of second step 80, an ECI range 84 is defined that correlates to a predetermined distance from the tissue 16. In an exemplary embodiment provided for illustrative purposes only, the predetermined distance is 2 mm, and so the ECI range 84 has a first threshold value 86 that corresponds to 0 mm from the tissue 16 (i.e., the electrode is in contact with the tissue), and a second threshold value 88 that corresponds to location that is 2 mm from the tissue 16. These thresholds may be set by either preprogramming them into the ECU 32, or a user may input them using a conventional I/O device. In a second substep 90 of second step 80, the calculated ECI is compared to the predefined ECI range 84. Based on this comparison, the relative proximity of the electrode 12 is determined.

More particularly, if the calculated ECI is within the range 84, then the electrode 12 is deemed to be in "close proximity" of the tissue 16. In this particular embodiment, if the electrode is within 0-2 mm of the tissue, it is deemed to be in "close proximity." If the calculated ECI falls below the first threshold value 86, then the electrode 12 is deemed to be in contact with the tissue 16. Finally, if the calculated ECI falls outside of the second threshold value 88, then the electrode 12 is deemed to not be in close proximity of the tissue 16, but rather is further away than the predetermined distance, which, in this embodiment would mean that the electrode 12 is further than 2 mm from the tissue 16. It should be noted that a range of 0-2 mm is used throughout as the range corresponding to "close proximity." However, this range is provided for exemplary purposes only and is not meant to be limiting in nature. Rather, any other ranges of distance from the tissue 16 may be used depending on the application.

Figure 8A:
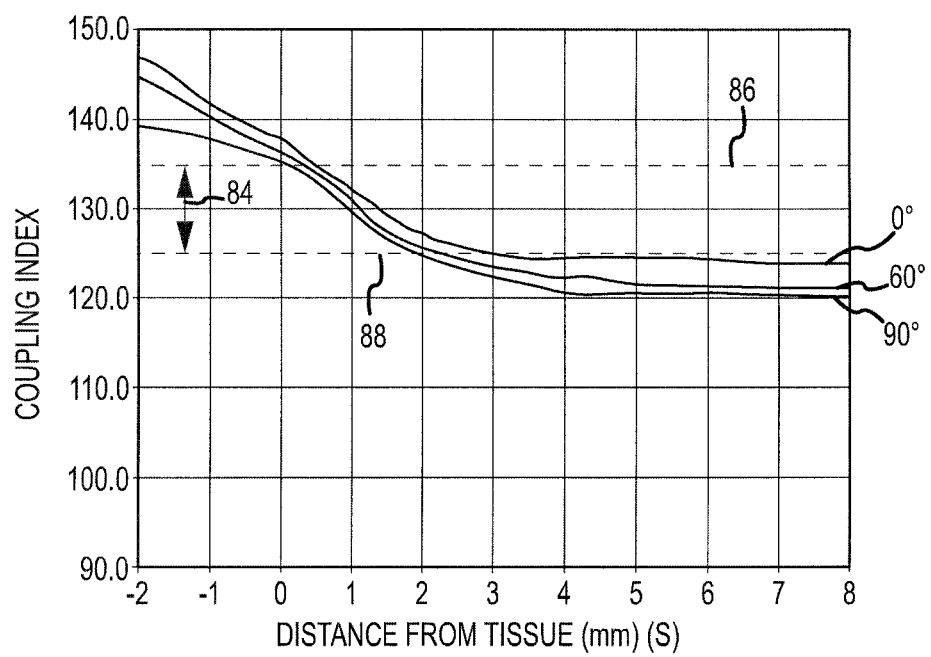
FIGS. 8a and 8b are charts illustrating the relationship of electrical coupling index (ECI) as a function of distance from tissue.
Figure 8B:
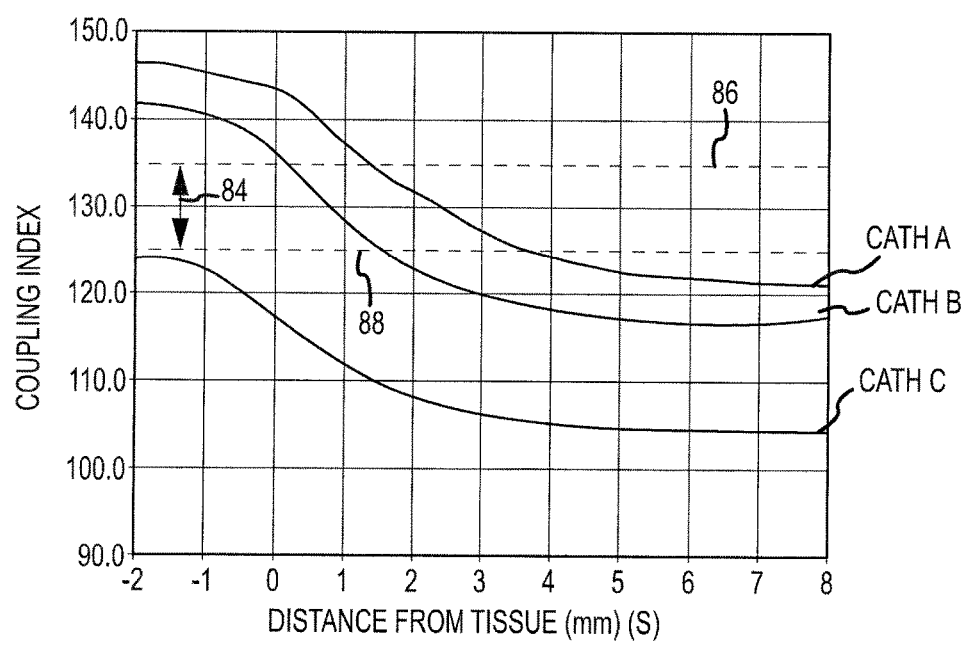

FIGS. 8a and 8b are provided to illustrate how the above described methodology may be applied. FIG. 8a illustrates examples of the results of ECI calculations that are meant to correspond to calculations representing three different angles of approach—0, 60, and 90 degrees—of the electrode 12 to the tissue 16. FIG. 8b illustrates examples of the results of ECI calculations that are meant to correspond to calculations resulting from the use of different types of catheters (i.e., CATH A, CATH B, and CATH C), which may influence the ECI calculations. It should be noted that the illustrated calculations do not correspond to actual test data or calculations made during an actual procedure, but rather are provided solely for illustrative purposes. In this example, the predetermined distance from the heart that is deemed to be "close proximity" was 0 to 2 mm.

As seen in FIG. 8a, in this particular example, the calculations for each angle of approach are fairly consistent with each other. As such, a single ECI range 84 may be defined that can be compared to any calculated ECI regardless of the angle of approach. In this particular example, the ECI range 84 is defined by the first threshold 86 of 135, which corresponds to 0 mm from the tissue 16, and the second threshold 88 of 125, which corresponds to 2 mm from the tissue 16. When the electrode is more than approximately 2 mm away from the tissue 16, the ECI is below 125, the second threshold 88 of the ECI range 84, and is relatively stable. As the electrode 12 approaches the tissue 16, however, the ECI begins to increase. When the electrode 12 is approximately 2 mm away, the ECI is around 125, which, again, is the second threshold 88 of the ECI range 84. As the electrode 12 continues to get closer the tissue 16, and therefore in closer proximity to the tissue 16, the ECI continues to increase. When the electrode 12 reaches the tissue 16 and makes contact, the ECI is at the first threshold 86 of approximately 135.

With respect to FIG. 8b, in this particular example, the illustrated calculations are spaced apart, as opposed to being closely grouped together. As such, a single ECI range 84 cannot be defined that would allow for the comparison with any calculated ECI. A number of factors may contribute to the spacing out of the calculations. For example, the type of catheter used, the particular environment in which the calculations are made, attributes of the patient, etc. may all contribute to the resulting spacing out of the calculations. To compensate for such factors, an offset is used. More particularly, if one or more contributory factors are present, the clinician is able to enter such information into the ECU 32 via a user interface for example, which will then be configured to add or subtract a defined offset from one or both of the calculated ECI and/or the ECI range. In an exemplary embodiment, ECU 32 may be programmed with one or more offsets, or the offset(s) may be entered by a user using a conventional I/O interface. Accordingly, in on exemplary embodiment, rather than simply comparing the ECI to an ECI range, an offset is added to or subtracted from either the ECI range, or to the calculated ECI itself. In either instance, the added or subtracted offset performs a scaling function that allows for the comparison described above to be made.

In the particular example illustrated in FIG. 8b, the ECI range 84 is a baseline ECI range defined by the first threshold 86 of 135, which corresponds to 0 mm from the tissue 16, and the second threshold 88 of 125, which corresponds to 2 mm from the tissue 16. If the particular procedure is one in which an offset would apply, the ECU 32 makes the necessary adjustments, and then the methodology continues as described above with respect to FIG. 7. When the electrode is more than approximately 2 mm away from the tissue 16, the ECI is below 125, the second threshold 88 of the ECI range 84, and is relatively stable. As the electrode 12 approaches the tissue 16, however, the ECI begins to increase. When the electrode 12 is approximately 2 mm away, the ECI is around 125, which, again, is the second threshold 88 of the ECI range 84. As the electrode 12 continues to get closer the tissue 16, and therefore in closer proximity to the tissue 16, the ECI continues to increase. When the electrode 12 reaches the tissue 16 and makes contact, the ECI is at the first threshold 86 of approximately 135.

Accordingly, by knowing the ECI (whether as calculated and/or with an offset) and comparing it to the ECI range representing a predetermined distance from the tissue 16 (which may include an offset depending on the circumstances), one can easily determine whether the electrode 12 is in contact with, in close proximity to, or far away from the heart tissue 16.

In another exemplary embodiment, rather than comparing a calculated finite ECI to a predefined range, the rate of change of the ECI $$\left(\text{i.e.,} \frac{dECI}{dt}\right)$$

may be evaluated and used to assess the proximity of the electrode 12 to the tissue 16. When the electrode 12 is within a predetermined distance from the tissue 16, the rate of change of the ECI or the change in the slope between ECIs over a predetermined amount of time $$\left(\text{i.e.,} \frac{d^2ECI}{dt^2}\right)$$

is most evident, and therefore, the rate of change in the ECI is greater than when either in contact with or far away from the tissue 16. Accordingly, it follows that when the rate of change of the ECI over a predetermined period of time is within a certain range or equals a particular rate, one may be able to determine whether the electrode 12 is within a predetermined distance or in close proximity to the tissue 16.

Figure 9:
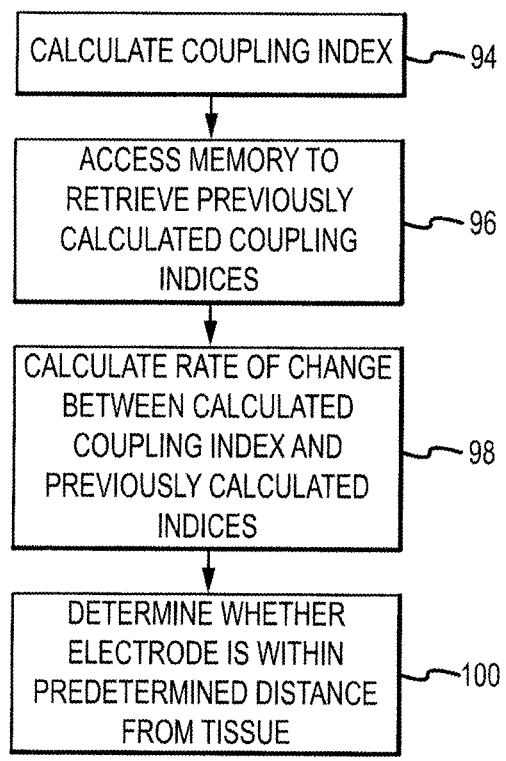
FIG. 9 is a flow diagram illustrative of another exemplary embodiment of a method for assessing the proximity of an electrode to tissue in accordance with present teachings.

FIG. 9 illustrates one exemplary embodiment of a methodology that uses the rate of change of the ECI. In this embodiment, a storage medium 92 (i.e., memory 92) is provided to store a predetermined number of previously calculated ECIs. The memory 92 may be part of the ECU 32 (See FIG. 1), or may be a separate component (or part of another component) that is accessible by the ECU 32 such that the ECU 32 may retrieve the stored ECIs. In an exemplary embodiment, the ECU 32 is configured to access the memory 92 and to calculate the rate of change in the ECI or the slope of a line drawn between a current or most recent ECI calculation and one or more previously calculated ECIs. If the rate of change or slope meets a predetermined value or falls with a predetermined or predefined range, then the ECU 32 will recognize that the ECI has changed at a certain rate, and therefore, that electrode 12 is within a certain distance of the tissue 16.

Accordingly, with specific reference to FIG. 9, in a first step 94 of this particular embodiment, a current ECI is calculated. In a second step 96, the ECU 32 accesses the memory 92 to retrieve one or more previously calculated ECIs. In a third step 98, the rate of change/slope between the current ECI and the one or more previously calculated ECIs is calculated. In a fourth step 100, the ECU 32 determines whether the electrode 12 is in close proximity to the tissue 16 based on the rate of change in the ECI.

This embodiment is particularly useful because the raw ECI is not being directly compared to a range of ECIs. Rather, because it is a rate of change or slope calculation, it does not matter what the magnitude of the ECI is, as it is the rate of change of the ECI that is being evaluated. Accordingly, it provides a more normalized approach for assessing proximity.

In an exemplary embodiment, whether the system 10 uses the raw ECI or the rate of change of the ECI to assess proximity, the system 10 is further configured to provide an indication to the clinician manipulating the catheter 14 or to a controller of a robotically controlled device that drives the catheter 14 that the electrode 12 is in "close proximity" to the tissue 16. In one exemplary embodiment, the ECU 32 is configured to generate a signal representative of an indicator that the electrode 12 is within the certain predetermined distance of the tissue 16 (e.g., 0-2 mm). In such an instance, this indicator indicates that the electrode 12 is in close proximity of the tissue 16 and allows the clinician or robotic controller to adjust its conduct accordingly (e.g., slow down the speed of approach). Such an indicator may be visually displayed on the display 34 of the system in the same manner described above with respect to the display of the ECI, may be displayed in a graphical form, may be in the form of an audible warning, or may comprise any other known indicators. With respect to robotic applications, the signal may be transmitted by the ECU 32 to a controller of the robotic device, which receives and processes the signal and then adjusts the operation of the robot as necessary. In other exemplary embodiments, the ECU 32 may also provide indicators that the electrode 12 is far away from the tissue 16 (i.e., further away than a predetermined distance), and/or that the electrode 12 is in contact with the tissue 16.

In another exemplary embodiment, the ECI may be used, in part, to calculate an electrical coupling index rate (ECIR). The resulting ECIR can, in turn, be used to assess the proximity of the electrode 12 to the tissue 16. In an exemplary embodiment, the ECU 32 is configured to calculate the ECIR, however, in other exemplary embodiments other processors or components may be used to perform the calculation. As will be described below, this particular embodiment provides a graded level of proximity.

In simple terms, the ECIR is calculated by dividing the change in ECI by the change in distance or position of the electrode 12 over a predetermined period of time. More specifically, the ECIR is calculated using the following equation (4):

$$ECIR := \frac{dECI}{ds} = \frac{dECI/d}{ds/dt} \qquad (4)$$

where "s" is the length of the path of the electrode in three-dimensional space (i.e., change in distance or position). The change in the ECI is calculated by sampling the ECI calculations performed by the ECU 32 (these calculations are described in great detail above) at a predetermined rate and then determining the difference between a current calculation and the most recent previous calculation, for example, that may be stored in a storage medium that is part of accessible by the ECU 32. In another exemplary embodiment, however, the difference may be between a current calculation and multiple previous calculations, or an average of previous calculations.

In an exemplary embodiment, the ECU 32 samples the calculated ECI every 10 to 30 ms, and then calculates the change in the ECI over that time interval $$\left(\text{i.e.,} \frac{dECI}{dt}\right).$$

It will be appreciated by those of ordinary skill in the art that the ECI may be sampled at rates other than that described above, and that such rates are provided for exemplary purposes only. For example, in another exemplary embodiment, using techniques well known in the art, the sampling is timed or synchronized to coincide with the cardiac cycle so as to always sample at the same point in the cardiac cycle, thereby avoiding variances due to the cardiac cycle. In another exemplary embodiment, the sampling of the ECI is dependent upon a triggering event, as opposed to being a defined time interval. For example, in one exemplary embodiment, the sampling of the ECI is dependent upon the change in the distance/position of the electrode 12 meeting a particular threshold. More particularly, when the system 10 determines that the electrode has moved a predetermined distance, the ECU 32 will then sample the ECI over the same period of time in which the electrode 12 moved. Accordingly, it will be appreciated by those of ordinary skill in the art that many different sampling rates and/or techniques may be employed to determine the change in the ECI.

With respect to the change in the distance (or position/location) of the electrode, this change may be calculated by the ECU 32 based on location coordinates provided to it by the system 30 (i.e., x, y, z coordinates provided by the mapping, visualization, and navigation system 30), or may be calculated by the system 30 and then provided to the ECU 32. As with the change in ECI calculation, the change in distance or location is determined by sampling the location coordinates of the electrode 12 at a predetermined rate. From this, the change in distance over time $$\left(\text{i.e., } \frac{ds}{dt}\right)$$

can be derived. In an exemplary embodiment, the location coordinates of the electrode 12 are sampled every 10 to 30 ms, and then the change in the location is calculated over that time interval. It will be appreciated by those of ordinary skill in the art that the location/position of the electrode may be sampled at rates other than that described above, and that such rates are provided for exemplary purposes only. For example, in another exemplary embodiment, using techniques well known in the art, the sampling is timed or synchronized to coincide with the cardiac cycle so as to always sample at the same point in the cardiac cycle, thereby avoiding variances due to the cardiac cycle.

Once these two "change" calculations are complete, the ECU 32 is able to calculate the ECIR by dividing the change in the ECI by the change in the distance or location of the electrode 12

$$\left(\text{i.e., } \frac{dECI}{ds}\right).$$

In an exemplary embodiment, the calculated ECIR is saved in a storage medium that is accessible by the ECU 32.

Figure 10:
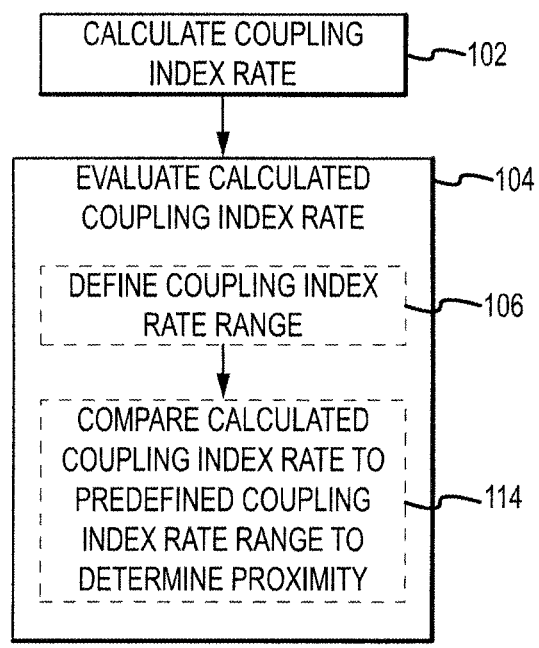
FIG. 10 is a flow diagram illustrative of yet another exemplary embodiment of a method for assessing the proximity of an electrode to tissue in accordance with present teachings.

Once the ECIR has been calculated, it may be used to assess, among other things, the proximity of the electrode 12 to the tissue 16. In an exemplary embodiment illustrated in FIG. 10, the ECIR is calculated in a first step 102. In a second step 104, the calculated ECIR is evaluated to determine whether the electrode 12 is within a predetermined distance from the tissue 16, in contact with the tissue 16, or further away from the tissue 16 than the predetermined distance.

More particularly, in a first substep 106 of step 104, a ECIR range 108 is defined that correlates to a predetermined distance from the tissue 16. In an exemplary embodiment provided for illustrative purposes only, the predetermined distance is 2 mm, and so the ECIR range 108 has a first threshold value 110 that corresponds to 0 mm from the tissue 16 (i.e., the electrode 12 is in contact with the tissue 16), and a second threshold value 112 that corresponds to a location that is 2 mm from the tissue 16. These thresholds may be set by either preprogramming them into the ECU 32, or a user may manually input them into the ECU 32 using a conventional I/O device.

In a second substep 114 of second step 104, the calculated ECIR is compared to the predefined range 108 of ECIRs. Based on this comparison, the relative proximity of the electrode 12 is determined. More particularly, if the calculated ECIR is within the range 108, then the electrode 12 is deemed to be in "close proximity" of the tissue 16. In this particular embodiment, if the electrode 12 is within 0-2 mm of the tissue 16, it is deemed to be in "close proximity." If the calculated ECIR falls below the first threshold value 110, then the electrode 12 is deemed to be in contact with the tissue 16. Finally, if the calculated ECIR falls outside of the second threshold value 112, then the electrode 12 is deemed to not be in close proximity of the tissue 16, but rather is further away than the predetermined distance, which, in this embodiment would mean that the electrode 12 is further than 2 mm from the tissue 16.

Figure 11:
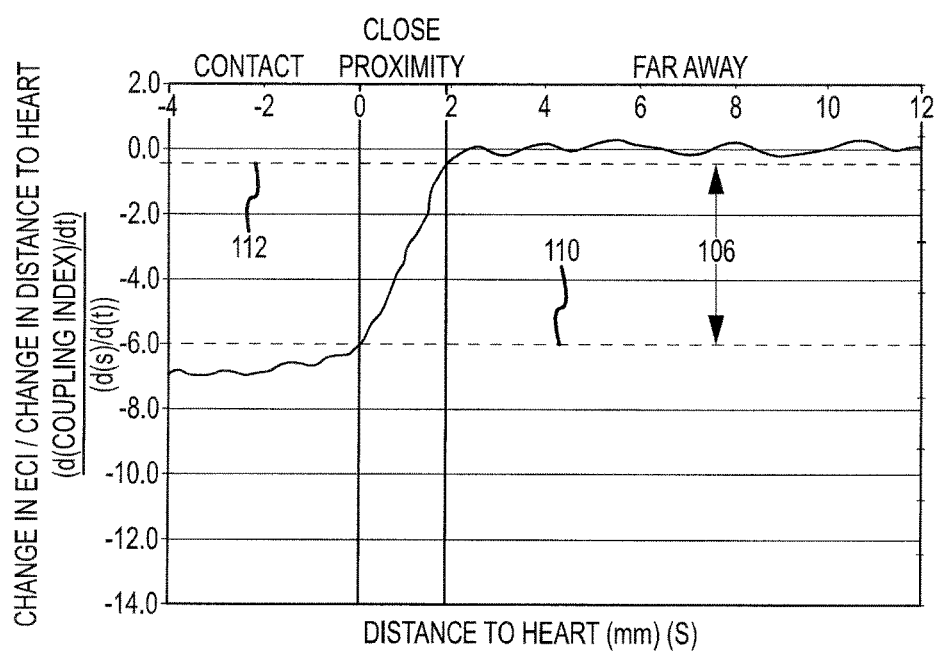
FIG. 11 is a chart illustrating the relationship of electrical coupling index rate (or ECIR) as a function of distance from tissue.

FIG. 11 is provided to show how the above described methodology may be applied, and illustrates what a ECIR calculation may look like. It should be noted that the illustrated calculations are not based on actual testing or ECIR calculations made during an actual procedure, but rather are provided solely for illustrative purposes. In this particular example, the ECIR range 108 is defined by a first threshold 110 of −6.0, which corresponds to 0 mm from the tissue 16, and a second threshold 112 of −0.5, which corresponds to 2 mm from the tissue 16. In this particular example, the predetermined distance from the heart that is deemed to be "close proximity" is 0-2 mm. It should be noted that the ECIR becomes negative as the tissue 16 is approached because as the electrode 12 comes closer to the tissue 16, the ECI increases. Accordingly, the value representing the change in ECI is negative since a higher ECI is subtracted from a lower ECI.

As seen in FIG. 11, in this example, when the electrode 12 is more than approximately 2 mm away from the tissue 16, the ECIR is close to zero (0) and relatively stable, but more particularly hovering between −0.5 and +0.5. This is partly because the further away from the tissue 16 the electrode 12 is, the ECIR is less responsive. However, as the electrode 12 approaches the tissue 16, the ECIR begins to decrease and becomes dramatically more dynamic. When electrode is approximately 2 mm away, the ECIR is around −0.5, which is the second threshold 112 of the ECIR range 108. As the electrode 12 continues to get closer the tissue 12, and therefore in closer proximity thereto, the ECIR continues to decrease. In this example, when the electrode 12 reaches the tissue 16 and makes initial contact, the ECIR is at −6.0, which is the first threshold 110 of the ECIR range 108. The ECIR then begins to stabilize at a level around −7.0 that is much lower than the level when the electrode is "far away" from the tissue (i.e., more than 2 mm) and outside of the predetermined ECIR range 108.

Accordingly, by knowing the ECIR and comparing that rate to a predefined ECIR range representing a predetermined distance from the tissue 16, one can easily determine whether the electrode 12 is in contact with, in close proximity to, or far away from the tissue 16.

Figure 12:
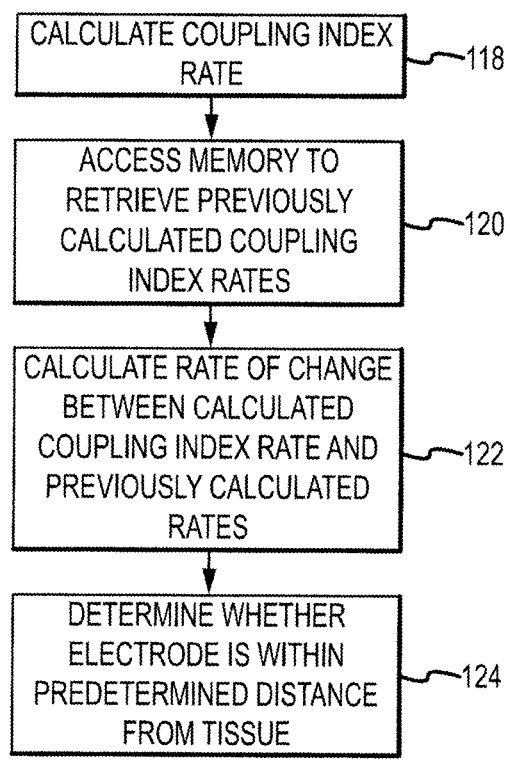
FIG. 12 is a flow diagram illustrative of yet another exemplary embodiment of a method for assessing the proximity of an electrode to tissue in accordance with present teachings.

With reference to FIG. 12, another exemplary embodiment of a method for assessing the proximity using the ECIR will be described. In this particular embodiment, rather than comparing a calculated finite ECIR to a predefined range, the rate of change of the ECIR $$\left(\text{i.e., } \frac{d}{dt}\left(\frac{dECI}{ds}\right) \text{ or } \frac{d^2ECI}{ds^2}\right)$$

is evaluated. It will be appreciated by those of ordinary skill in the art that the rate of change in the ECIR may be with respect to time or space. Accordingly, both the temporal and spatial approaches will be described below. By evaluating the rate of change in the ECIR, a more robust and accurate proximity assessment can be performed More specifically, when the electrode 12 is within a predetermined distance from the tissue 16, the rate of change in the ECIR, or change in the slope between ECIRs over a predetermined period of time, is greater than when the electrode 12 is either in contact with or far away from the tissue 16. (See FIG. 11, for example). Accordingly, it follows that when the rate of change of the ECIR over a predetermined period of time is within a certain range or equals particular rate that may be preprogrammed into the ECU 32 or input by a user as described above, one may be able to determine whether the electrode is within a predetermined distance or in close proximity to the tissue. The methodology of this particular embodiment may carried out using either one of the calculations represented by equation (5) or equation (6) below:

$$\text{Rate of Change of } ECIR = \frac{d}{dt}\left(\frac{dECI}{ds}\right) \quad (5)$$

$$\text{Rate of Change of } ECIR = \frac{d/dt(dECI/ds)}{ds/dt} = \frac{d^2ECI}{ds^2} \quad (6)$$

With reference to FIG. 12, in an exemplary embodiment, the rate of change in the ECIR may be determined by simply calculating the change between two or more ECIR calculations (i.e., equation (5) above). In such an embodiment, a storage medium 116 (i.e., memory 116) is provided to store a predetermined number of previously calculated ECIRs. The memory 116 may be part of the ECU 32 (See FIG. 1), or may be a separate component (or part of another component) that is accessible by the ECU 32 such that the ECU 32 may retrieve the stored ECIRs. In an exemplary embodiment, the ECU 32 is configured to access the memory 116 and to calculate the rate of change of the ECIR or slope of a line drawn between a current or most recent ECIR calculation and one or more prior ECIR calculations. If the rate of change or slope meets a predetermined value or falls with a predetermined range, then the ECU 32 will recognize that the ECIR has changed a certain amount, and therefore, that electrode 12 is within a certain distance of the tissue 16.

Accordingly, with reference to FIG. 12, in a first step 118 of this particular embodiment, a current ECIR is calculated. In a second step 120, the ECU 32 accesses the memory 116 to retrieve one or more previously calculated ECIRs. In a third step 122, the rate of change or the slope between the current ECIR and one or more previously calculated ECIRs is calculated. In a fourth step 124, the ECU 32 determines whether the electrode 12 is in close proximity to the tissue 16 based on the rate of change in the ECIR.

In another exemplary embodiment of a methodology based on a rate of change in ECIR, small changes in the location or position of the electrode 12, and therefore, the corresponding rate of change of the corresponding ECIR, can be taken advantage of to obtain a substantially continuous and robust assessment of proximity between the electrode 12 and the tissue 16.

More particularly, perturbations can be induced or instigated in the position of the electrode 12 either manually by a clinician or by way of a robotic controller. These small changes in position of the electrode 12 (e.g., on the order of 0.2 mm) can be measured by system 30, as described above, and processed, at least in part, with the corresponding change in the ECI and the change in position of the electrode 12 by the ECU 32, for example, to calculate the rate of change of the ECIR. The frequency of these perturbations may be sufficiently high to allow for the effective filtering or smoothing out of errors in the ECIR calculations. This may be beneficial for a number of reasons, such as, for example, to resolve environmental events such as cardiac cycle mechanical events. In such an instance, the perturbation frequency would be higher than the frequency of the cardiac cycle. In one exemplary embodiment, the frequency of the perturbations is five to ten perturbations per second. Accordingly, the cardiac frequency may be filtered out of, or compensated for, in the calculations so as to smooth out any changes resulting during the cardiac cycle because of the constant movement of the electrode.

Alternatively, if the perturbations occur less frequently, the inducement of the perturbations may be synchronized with or coordinated to occur at one or more points in the cardiac cycle using known methodologies. By doing so, the filtering or smoothing effect described above may be carried out and also allow for the observation of proximity changes as a result of catheter or electrode movement/manipulation or ventilation, for example. Accordingly, the inducement of perturbations and the resulting ECIR resulting from such perturbations can be used to filter or smooth variation in signals resulting from cardiac cycle mechanical events, thereby providing a more robust system.

Accordingly, in this particular aspect of the invention, fast perturbations of the catheter, and therefore, the electrode, permit frequent determinations of ECIR. At a separate and slower time scale, motions of the catheter and the electrode towards or away from the tissue permit a filtered derivative of ECIR. Changes over this longer time scale of the gradual distance toward or away from the tissue allow for a good determination of a second spatial derivative of ECI $$\left(\text{i.e., } \frac{d^2ECI}{ds^2} = \frac{d/dt(ECIR)}{ds/dt}\right).$$

Figure 13:
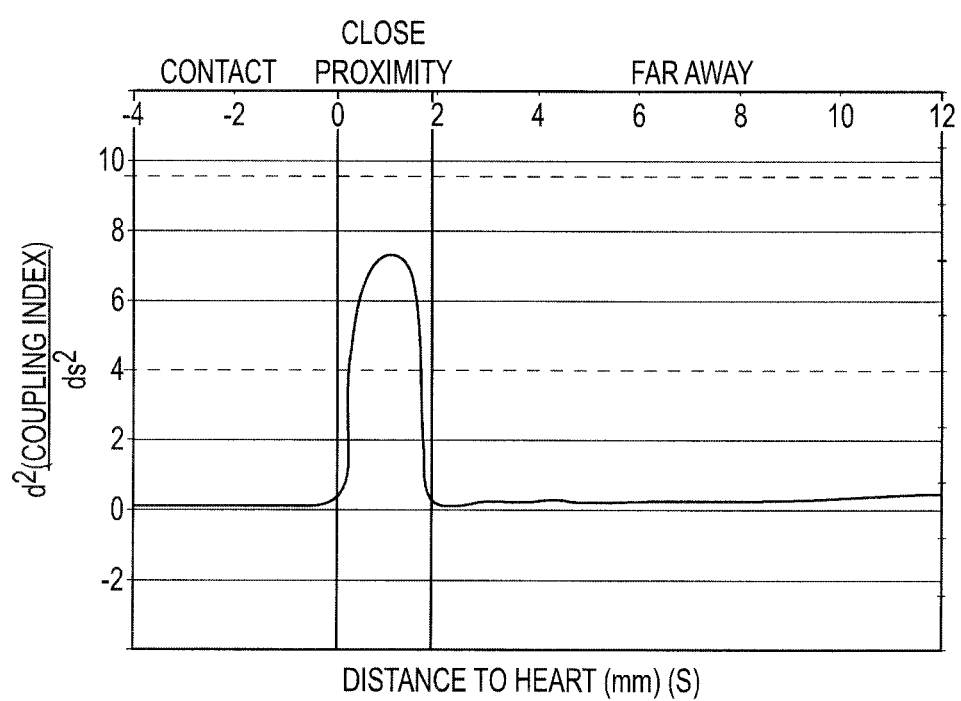
FIG. 13 is a chart illustrating an example employing a method of proximity assessment involving a two-time scale approach.

Accordingly, this particular methodology represents a two time-scale approach (i.e., fast perturbations of the electrode 12 combined with slow movement of the electrode 12 towards the tissue 16). FIG. 13 illustrates an exemplary representation of what the output of this methodology looks like, which provides a sound representation of proximity. Such a methodology results in a more robust discriminator of proximity.

Whether the calculated ECIR is compared to a predetermine range of ECIRs, or the rate of change of the ECIR is evaluated to assess the proximity of the electrode 12 to the tissue 16, in an exemplary embodiment, the system 10 may provide an indication to the clinician manipulating the catheter 14 or to a controller of a robotically controlled device that drives the catheter 14 that the electrode is in "close proximity" to the tissue 16. In one exemplary embodiment, the ECU 32 is configured to generate a signal representative of an indicator that the electrode 12 is within the certain predetermined distance of the tissue 16 (e.g., 0-2 mm). In such an instance, this indicator indicates that the electrode 12 is in close proximity to the tissue 16 and allows the clinician or robotic controller to adjust its conduct accordingly (e.g., slow down the speed of approach). Such an indicator may be visually displayed on the display 34 of the system in the same manner described above with respect to the display of the ECI, may be displayed in graphical form, may be in the form of an audible warning, or may comprise any other known indicators. With respect to robotic applications, the signal may be transmitted by the ECU 32 to a controller from the robotic device, which receives and processes the signal and then adjusts the operation of the robot as necessary. In other exemplary embodiments, the ECU 32 may also provide indicators that the electrode 12 is far away from the tissue (i.e., further away than a predetermined distance), and/or that the electrode 12 is in contact with the tissue.

Additionally, whether the ECI or the ECIR are used to determine or assess the proximity of the electrode to the tissue, in an exemplary embodiment, the ECU 32 is programmed with a computer program (i.e., software) encoded on a computer storage medium for assessing and/or determining the proximity of the electrode 12 to the tissue 16. In such an embodiment, the program generally includes code for calculating a ECI responsive to values for first and second components of the complex impedance between the catheter electrode 12 and the tissue 16, and also code to process ECI in the various ways described above (i.e., comparison of ECI to a predefined range, calculating ECIRs and comparing calculated ECIR to predefined ranges, calculating rate of change in the ECI and evaluating the same, and calculating rate of change in ECIR and evaluating the same, for example).

Figure 14:
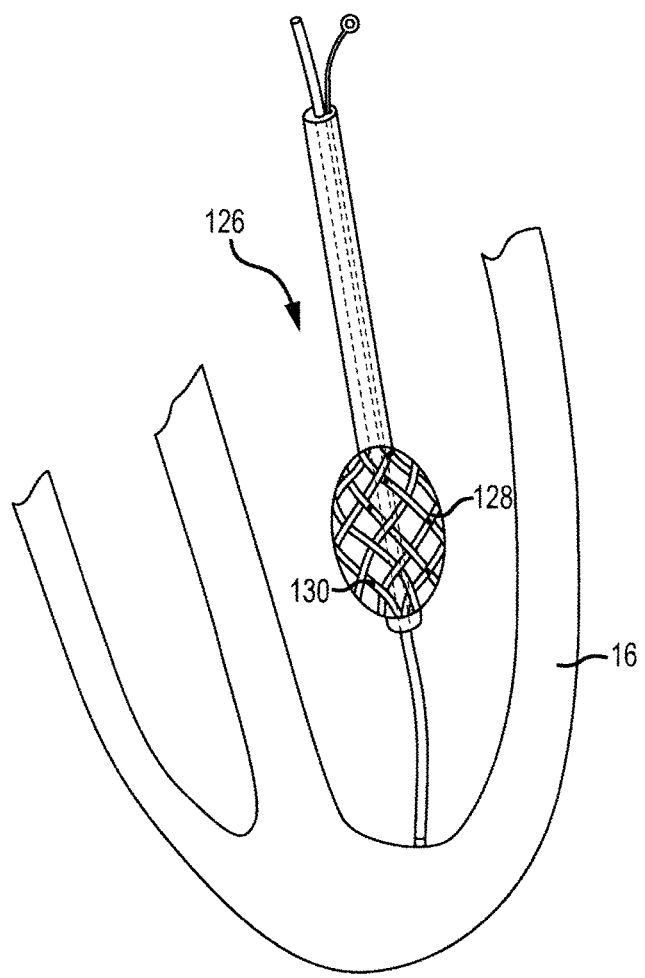
FIG. 14 is diagrammatic view of a multi-electrode, array catheter illustrating one embodiment of a system in accordance with present teachings.

The present invention may also find application in systems having multiple electrodes used for mapping the heart or other tissues, obtaining electrophysiological (EP) information about the heart or other tissues or ablating tissue. Referring to FIG. 14, one example of an EP catheter 126 is shown. The EP catheter 126 may be a non-contact mapping catheter such as the catheter sold by St. Jude Medical, Atrial Fibrillation Division, Inc. under the registered trademark "ENSITE ARRAY." Alternatively, the catheter 126 may comprise a contact mapping catheter in which measurements are taken through contact of the electrodes with the tissue surface. The catheter 126 includes a plurality of EP mapping electrodes 128. The electrodes 128 are placed within electrical fields created in the body 17 (e.g., within the heart). The electrodes 128 experience voltages that are dependent on the position of the electrodes 128 relative to the tissue 16. Voltage measurement comparisons made between the electrodes 128 can be used to determine the position of the electrodes 128 relative to the tissue 16. The electrodes 128 gather information regarding the geometry of the tissue 16 as well as EP data. For example, voltage levels on the tissue surface over time may be projected on an image or geometry of the tissue as an activation map. The voltage levels may be represented in various colors and the EP data may be animated to show the passage of electromagnetic waves over the tissue surface. Information received from the electrodes 128 can also be used to display the location and orientation of the electrodes 128 and/or the tip of the EP catheter 126 relative to the tissue 16. The electrodes 128 may be formed by removing insulation from the distal end of a plurality of braided, insulated wires 130 that are deformed by expansion (e.g., through use of a balloon) into a stable and reproducible geometric shape to fill a space (e.g., a portion of a heart chamber) after introduction into the space.

In the case of contact mapping catheters, the ECI can be used to determine which the electrodes 128 are in contact with or in close proximity to the tissue 16 so that only the most relevant information is used in mapping the tissue 16 or in deriving EP measurements or so that different data sets are more properly weighted in computations. As with the systems described hereinabove, the signal source 61 of the sensing circuit 26 may generate excitation signals across source connectors SOURCE (+) and SOURCE (−) defined between one or more electrodes 128 and the patch electrode 22. The impedance sensor 58 may then measure the resulting voltages across sense connectors SENSE (+) and SENSE (−)) defined between each electrode 128 and the patch electrode 20. The ECU 32 may then determine which the electrodes 128 have the highest impedance and/or ECI to determine the most relevant electrodes 128 for purposes of mapping or EP measurements. Similarly, in the case of a multiple electrode ablation catheter (not shown), the ECI can be used to determine which electrodes are in contact with the tissue 16 so that ablation energy is generated through only those electrodes, or can be used to adjust the power delivered to different electrodes to provide sufficient power to fully ablate the relevant tissue.

The present invention also permits simultaneous measurements by multiple electrodes 128 on the catheter 126. Signals having distinct frequencies or multiplexed in time can be generated for each electrode 128. In one constructed embodiment, for example, signals with frequencies varying by 500 Hz around a 20 kHz frequency were used to obtain simultaneous distinct measurements from multiple electrodes 128. Because the distinct frequencies permit differentiation of the signals from each electrode 128, measurements can be taken for multiple electrodes 128 simultaneously thereby significantly reducing the time required for mapping and/or EP measurement procedures. Microelectronics permits precise synthesis of a number of frequencies and at precise quadrature phase offsets necessary for a compact implementation of current sources and sense signal processors. The extraction of information in this manner from a plurality of transmitted frequencies is well known in the field of communications as quadrature demodulation. Alternatively, multiple measurements can be accomplished essentially simultaneously by multiplexing across a number of electrodes with a single frequency for intervals of time less than necessary for a significant change to occur.

Although several embodiments of this invention have been described above with a certain degree of particularity, those skilled in the art could make numerous alterations to the disclosed embodiments without departing from the scope of this invention. All directional references (e.g., upper, lower, upward, downward, left, right, leftward, rightward, top, bottom, above, below, vertical, horizontal, clockwise and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not as limiting. Changes in detail or structure may be made without departing from the invention as defined in the appended claims.

What is claimed is:

1. A system for assessing the proximity of an electrode to a tissue in a body, comprising:
    a tissue sensing circuit configured to resolve a detected impedance into first and second components of a complex impedance between said electrode and said tissue, said tissue sensing circuit including a tissue sensing signal source configured to generate an excitation signal to be applied to said tissue and a complex impedance sensor coupled to said tissue sensing signal source and configured to measure a response signal and output said first and second components of said complex impedance; and
    an electronic control unit (ECU) configured to execute a computer program for assessing said proximity that is configured to:
        (i) acquire a plurality of values for said first and second components of said complex impedance from said tissue sensing circuit between said electrode and said tissue as said electrode moves in the body and to calculate a respective electrical coupling index (ECI) for each of said plurality of values of said first and second components of said complex impedance;
        (ii) process plural values of said electrical coupling index to determine a respective proximity of said electrode to said tissue as said electrode moves in the body, wherein said ECU, based on said ECI, is configured to determine whether said electrode is deemed not to be in contact with said tissue with said electrode being no more than a predetermined distance from said tissue wherein said predetermined distance is a positive, non-zero distance, said ECU, based on said ECI, being further configured to determine whether said electrode is deemed not to be in contact with said tissue with said electrode being beyond said predetermined distance from said tissue
    said ECU being further configured to generate a signal representative of an indicator of proximity between said electrode and said tissue and to transmit said generated signal to at least one of (i) an application and (ii) a device other than said tissue sensing circuit and said proximity assessing program, for control of said at least one of said application and said device.

2. The system of claim 1, wherein said ECU is further configured to
    (i) receive location coordinates corresponding to a location of said electrode within said body;
    (ii) calculate a change in said ECI over a predetermined time interval;
    (iii) calculate a change in said location coordinates of said electrode over said predetermined time interval; and
    (iv) calculate an electrical coupling index rate (ECIR) by dividing said change in ECI by said change in said location coordinates of said electrode.

3. The system of claim 2, wherein said ECU is further configured to compare said ECIR with a predetermined range of ECIRs to determine whether said electrode is within said predetermined distance from said tissue, said predetermined range being defined by a first ECIR threshold indicative of said electrode being in contact with said tissue and a second ECIR threshold indicative of said electrode being said predetermined distance away from said tissue.

4. The system of claim 2 further comprising a storage medium configured to store a plurality of previously calculated ECIRs, said storage medium being accessible by said ECU.

5. The system of claim 4, wherein said ECU is configured to calculate a rate of change of said ECIR between at least one of said plurality of previously calculated ECIRs and a current calculated ECIR over a predetermined period of time, and to determine the proximity of said electrode to said tissue based on said rate of change of said ECIR.

6. The system of claim 2, wherein said ECU is further configured to filter said ECIR calculation in response to induced perturbations in the location of said electrode.

7. The system of claim 2, wherein said ECU is further configured to calculate a second spatial derivative of said ECI by calculating a change in said ECIR as a result of perturbations in the position of said electrode over said change in location of said electrode and over said predetermined time interval, and to determine the proximity of said electrode to said tissue based on said second spatial derivative.

8. The system of claim 1, wherein said ECU is further configured to compare said calculated ECI with a predetermined range of ECIs to determine whether said electrode is no more than said predetermined distance from said tissue, said predetermined ECI range being defined by a first ECI threshold indicative of said electrode being in contact with said tissue, and a second ECI threshold indicative of said electrode being said predetermined distance away from said tissue.

9. The system of claim 1 further comprising a storage medium configured to store a plurality of previously calculated ECIs, said storage medium being accessible by said ECU.

10. The system of claim 9, wherein said ECU is configured to calculate a rate of change in said ECI between at least one of said plurality of previously calculated ECIs and a current calculated ECI, and to determine the proximity of said electrode to said tissue based on said rate of change of said coupling index.

11. The system of claim 1 wherein said one of said application and device comprises a display monitor, said ECU further configured to control said display monitor to visually display said indicator represented by said signal.

12. The system of claim 11 wherein said visual display of said indicator is selected from the group comprising a meter and a beacon.

13. The system of claim 12 wherein said electrode is displayed on said display monitor as said beacon whose appearance changes depending on the value of said ECI.

14. The system of claim 13 wherein a color of said beacon changes depending on the value of said ECI.

15. The system of claim 1, wherein said one of said application and device comprises a robotics application, and wherein said ECU is further configured to transmit said generated signal to a controller for said robotics application.

16. The system of claim 1 wherein said first and second components of said complex impedance comprises resistance and reactance, and wherein said electrical coupling index corresponds to a combination of a first term including resistance and independent of reactance and a second term including reactance and independent of resistance.

17. The system of claim 1 wherein said ECU via said proximity assessing program is configured to determine when said electrode is deemed in contact with said tissue, and wherein said at least one of said application and device controls the generation of ablation energy for or adjusts the power delivered to said electrode.

18. The system of claim 1 wherein said ECU via said proximity assessing program is configured to determine when said electrode is deemed in contact with or in close proximity to said tissue for purposes of enabling one of mapping and electrophysiological (EP) measurements via said electrode.

19. The system of claim 18 wherein said ECU is connected to a visualization, mapping, and navigation apparatus for making said mapping and EP measurements.

20. The system of claim 1 wherein said excitation signal has a frequency within a range of about 2 kHz to 200 kHz and wherein said complex impedance sensor includes a bandpass filter configured to permit an excitation frequency of said excitation signal to pass, said bandpass filter being further configured to block frequencies other than said excitation frequency.

21. An article of manufacture, comprising:
a non-transitory computer storage medium having a computer program encoded thereon for assessing the proximity of an electrode to a tissue in a body, said computer program including code for:
  (i) calculating a respective electrical coupling index (ECI) responsive to a plurality of values for first and second components of a complex impedance between said electrode and said tissue as said electrode moves in the body; and
  (ii) processing plural values of said calculated ECI to determine a respective proximity of said electrode to said tissue as said electrode moves in the body, said computer program further including code for determining, based on said ECI, whether said electrode is deemed not to be in contact with said tissue with said electrode being no more than a predetermined distance from said tissue, wherein said predetermined distance is a positive, non-zero distance, said computer program further including code for determining, based on said ECI, whether said electrode is deemed not to be in contact with said tissue with said electrode being beyond said predetermined distance from said tissue, and generating a signal representative of an indicator of proximity between said electrode and said tissue and transmitting said generated signal to at least one of (i) an application and (ii) a device other than said program, for control of said at least one of said application and device, wherein said at least one of said application and said device comprises a display monitor, said computer program further including code for controlling said display monitor to visually display said indicator of proximity represented by said generated signal.

22. The article of manufacture of claim 21 wherein said computer program includes code for
  (i) calculating a change in said ECI over a predetermined time interval;
  (ii) calculating a change in location coordinates of said electrode over said predetermined time interval; and
  (iii) calculating an electrical coupling index rate (ECIR) by dividing said change in ECI by said change in said location coordinates of said electrode.

23. The article of manufacture of claim 22 wherein said computer program further includes code for comparing said calculated ECIR with a predetermined range of ECIRs to determine whether said electrode is no more than said predetermined distance from said tissue, said predetermined ECIR range being defined by a first threshold ECIR indicative of said electrode being in contact with said tissue and a second threshold ECIR indicative of said electrode being said predetermined distance away from said tissue.

24. The article of manufacture of claim 22 wherein said computer program further includes code for calculating a rate of change in said ECIR between at least one of a plurality of previously calculated ECIRs and a current calculated ECIR, and to determine the proximity of said electrode to said tissue based on said rate of change in said ECIR.

25. The article of manufacture of claim 22 wherein said computer program further includes code for filtering said ECIR calculation in response to induced perturbations in the location of said electrode.

26. The article of manufacture of claim 22 wherein said computer program further includes code for calculating a second spatial derivative of said ECI by calculating a change in said ECIR as a result of perturbations in the position of said electrode over said change in location of said electrode and over said predetermined time interval to determine the proximity of said electrode to said tissue based on said second spatial derivative.

27. The article of manufacture of claim 21 wherein said computer program further includes code for comparing said calculated ECI with a predetermined range of ECIs to determine whether said electrode is no more than said predetermined distance from said tissue, said predetermined coupling index range being defined by a first ECI threshold indicative of said electrode being in contact with said tissue and a second ECI threshold indicative of said electrode being said predetermined distance away from said tissue.

28. The article of manufacture of claim 21 wherein said computer program further includes code for calculating a rate of change in said ECI between at least one of a plurality of previously calculated ECIs and a current calculated ECI, and for determining the proximity of said electrode to said tissue based on said rate of change in said ECI.

29. The article of manufacture of claim 21 wherein said one application and device comprises a robotics application, and wherein said computer program further includes code for transmitting said generated signal to a controller for said robotics application.

30. The article of manufacture of claim 21 wherein said computer program further includes code to visually display said indicator selected from the group comprising a meter and a beacon.

31. The article of manufacture of claim 30 wherein said computer program further includes code to change an appearance of said beacon depending on the value of said ECI.

32. The article of manufacture of claim 30 wherein said computer program further includes code to change a color of said beacon depending on the value of said ECI.

33. A method for assessing the proximity of an electrode to a tissue in a body, comprising:
resolving, using a tissue sensing circuit, a detected impedance into first and second components of a complex impedance between said electrode and said tissue by generating, using a tissue sensing signal source of said tissue sensing circuit, an excitation signal to be applied to said tissue and measuring, using a complex impedance sensor coupled to said tissue sensing signal source, a response signal;

acquiring a plurality of values for said first and second components of said complex impedance between said electrode and said tissue as said electrode moves in the body;

calculating, using an electronic control unit, a respective electrical coupling index (ECI) for each of said plurality of values of said first and second components of said complex impedance; and processing, using said electronic control unit, plural values of said calculated ECI to determine a respective proximity of said electrode to said tissue as said electrode moves in the body, wherein said electronic control unit, based on said ECI, is configured to determine whether said electrode is deemed not to be in contact with said tissue with said electrode being no more than a predetermined distance from said tissue, wherein said predetermined distance is a positive, non-zero distance, said electronic control unit, based on said ECI, is further configured to determine whether said electrode is deemed not to be in contact with said tissue with said electrode being beyond said predetermined distance from said tissue, said electronic control unit generating a signal representative of an indicator of proximity between said electrode and said tissue and transmitting said generated signal to at least one of (i) an application and (ii) a device, for control of said at least one of said application and said device.

34. The method of claim 33 further comprising:
receiving location coordinates corresponding to a location of said electrode within said body;
calculating a change in said ECI over a predetermined time interval;
calculating a change in location coordinates of said electrode over said predetermined time interval; and
calculating an electrical coupling index rate (ECIR) by dividing said change in ECI by said change in said location coordinates of said electrode.

35. The method of claim 34 further comprising comparing said calculated ECIR with a predetermined predefined range of ECIRs to determine whether said electrode is no more than said predetermined distance from said tissue, said predetermined ECIR range being defined by a first ECIR threshold indicative of said electrode being in contact with said tissue and a second ECIR threshold indicative of said electrode being said predetermined distance away from said tissue.

36. The method of claim 34 further comprising calculating a slope between at least one of a plurality of previously calculated ECIRs and a current calculated ECIR, and determining the proximity of said electrode to said tissue based on said slope calculation.

37. The method of claim 34 further comprising:
inducing perturbations in the position of said electrode;
calculating a second derivative of said ECI by calculating a change in said ECIR as a result of said perturbations over said change in location of said electrode and over said predetermined time interval; and determining the proximity of said electrode to said tissue based on said second spatial derivative.

38. The method of claim 33 further comprising comparing said calculated ECI with a predetermined range of ECIs to determine whether said electrode is no more than said predetermined distance from said tissue, said predetermined ECI range being defined by a first ECI threshold indicative of said electrode being in contact with said tissue and a second ECI range threshold indicative of said electrode being said predetermined distance away from said tissue.

39. The method of claim 33 further comprising calculating a slope of a line between at least one of a plurality of previously calculated ECIs and a current calculated ECI, and determining the proximity of said electrode to said tissue based on said slope calculation.

40. The method of claim 33 wherein said generated signal is representative of an indicator that said electrode is within said predetermined distance from said tissue.

41. The method of claim 40 further comprising displaying said indicator represented by said signal on a display monitor.

42. The method of claim 40 wherein said at least one of said application and device comprises a robotics application, said method further comprising transmitting said generated signal to a controller for said robotics application.

43. A system for assessing the proximity of an electrode to a tissue in a body, comprising:
a tissue sensing circuit configured to resolve a detected impedance into first and second components of a complex impedance between said electrode and said tissue, said tissue sensing circuit being configured to generate an excitation signal to be applied to said tissue and to measure a response signal; and
an electronic control unit (ECU) configured to execute a computer program for assessing said proximity that is configured to:
(i) acquire a plurality of values for said first and second components of said complex impedance between said electrode and said tissue as said electrode moves in the body and to calculate a respective electrical coupling index (ECI) for each of said plurality of values of said first and second components of said complex impedance;
(ii) process plural values of said electrical coupling index to determine a respective proximity of said electrode to said tissue as said electrode moves in the body, wherein said ECU, based on said ECI, is configured to determine whether said electrode is deemed not to be in contact with said tissue with said electrode being no more than a predetermined distance from said tissue wherein said predetermined distance is a positive, non-zero distance, said ECU, based on said ECI, being further configured to determine whether said electrode is deemed not to be in contact with said tissue with said electrode being beyond said predetermined distance from said tissue, said ECU being further configured to generate a signal representative of an indicator of proximity between said electrode and said tissue and to transmit said generated signal to at least one of (i) an application and (ii) a device other than said tissue sensing circuit and said proximity assessing program, for control of said at least one of said application and said device;
wherein said one of said application and device comprises a robotics application, and wherein said ECU is further configured to transmit said generated signal to a controller for said robotics application; and
wherein said robotics application is configured to drive a catheter comprising said electrode, said controller of said robotics application being configured to adjust a speed of approach of said catheter in response to said generated signal.

44. The system of claim 43 wherein said speed adjustment comprises a reduction in speed.

* * * * *